(12) United States Patent
Pugia et al.

(10) Patent No.: US 8,865,648 B2
(45) Date of Patent: Oct. 21, 2014

(54) MONOMERIC AND DIMERIC FORMS OF ADIPONECTIN RECEPTOR FRAGMENTS AND METHODS OF USE

(75) Inventors: Michael J. Pugia, Granger, IN (US); Rui Ma, Mishawaka, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 13/265,968

(22) PCT Filed: Apr. 13, 2010

(86) PCT No.: PCT/US2010/030836
§ 371 (c)(1),
(2), (4) Date: Oct. 25, 2011

(87) PCT Pub. No.: WO2010/123720
PCT Pub. Date: Oct. 28, 2010

(65) Prior Publication Data
US 2012/0135916 A1    May 31, 2012

Related U.S. Application Data

(60) Provisional application No. 61/171,979, filed on Apr. 23, 2009.

(51) Int. Cl.
| | | |
|---|---|---|
| A61K 38/00 | (2006.01) |
| A61K 38/26 | (2006.01) |
| A61K 38/22 | (2006.01) |
| C07K 14/605 | (2006.01) |
| A61K 38/28 | (2006.01) |
| C07K 14/575 | (2006.01) |
| C07K 7/06 | (2006.01) |
| C07K 7/02 | (2006.01) |
| C07K 7/64 | (2006.01) |
| C07K 11/00 | (2006.01) |
| C07K 14/47 | (2006.01) |
| C07K 14/785 | (2006.01) |
| A61K 39/00 | (2006.01) |
| C07K 14/005 | (2006.01) |
| G01N 33/574 | (2006.01) |

(52) U.S. Cl.
CPC ........ G01N 33/574 (2013.01); G01N 33/57415 (2013.01); *G01N 2333/575* (2013.01)
USPC .......... 514/6.9; 514/6.7; 514/21.1; 514/21.3; 530/321; 530/323; 530/324

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,242,828 A | 9/1993 | Bergstrom et al. | |
| 5,719,060 A | 2/1998 | Hutchens et al. | |
| 5,831,012 A | 11/1998 | Nilsson et al. | |
| 6,124,137 A | 9/2000 | Hutchens et al. | |
| 6,225,047 B1 | 5/2001 | Hutchens et al. | |
| 6,329,209 B1 | 12/2001 | Wagner et al. | |
| 6,461,821 B1 | 10/2002 | Matsuzawa et al. | |
| 7,108,972 B2 | 9/2006 | Pena et al. | |
| 7,435,808 B2 | 10/2008 | Wu et al. | |
| 8,017,573 B2 * | 9/2011 | Pugia et al. .................... | 514/6.7 |
| 2002/0173474 A1 | 11/2002 | Schreiber et al. | |
| 2003/0083261 A1 | 5/2003 | Yu et al. | |
| 2003/0153013 A1 | 8/2003 | Huang | |
| 2004/0038428 A1 | 2/2004 | MacBeth et al. | |
| 2004/0241802 A1 | 12/2004 | Kadowaki et al. | |
| 2005/0032166 A1 | 2/2005 | Chen et al. | |
| 2005/0048565 A1 | 3/2005 | Tomita et al. | |
| 2005/0054005 A1 | 3/2005 | Ellis et al. | |
| 2007/0037207 A1 | 2/2007 | Tachikawa et al. | |
| 2007/0037226 A1 | 2/2007 | Golz et al. | |
| 2007/0042424 A1 | 2/2007 | Ebinuma et al. | |
| 2007/0053913 A1 | 3/2007 | Golz et al. | |
| 2008/0221305 A1 * | 9/2008 | Chen et al. .................... | 530/350 |
| 2009/0143275 A1 | 6/2009 | Pugia et al. | |
| 2010/0143958 A1 | 6/2010 | Pugia | |

FOREIGN PATENT DOCUMENTS

| | | |
|---|---|---|
| JP | 2007-506951 A | 3/2007 |
| JP | 2007-111050 A | 5/2007 |
| WO | WO 99/51773 | 10/1999 |
| WO | WO 00/56934 | 9/2000 |
| WO | WO 01/12662 | 2/2001 |
| WO | WO 01/90304 | 11/2001 |

(Continued)

OTHER PUBLICATIONS

Yamauchi et al., "Cloning of adiponectin receptors that mediate antidiabetic metabolic effects," Nature 423:762-769 (2003).*

(Continued)

*Primary Examiner* — James H Alstrum Acevedo
*Assistant Examiner* — Thea D'Ambrosio
(74) *Attorney, Agent, or Firm* — Kevin Stein

(57) ABSTRACT

Methods are disclosed for determining progression of a condition, onset of a condition, or efficacy of treatment of a condition characterized by an adipocyte imbalance in a patient. In addition, methods are disclosed of treating diabetes, abnormal adipocyte activity, and insulin resistance using monomeric, homodimeric, and heterodimeric forms of certain C-terminal fragments of adiponectin receptor. In addition, methods of treating abnormal adipocyte activity, treating metabolic syndrome, causing insulin secretion, increasing insulin levels, inhibiting insulin degradation enzyme, treating Alzheimer's disease, treating cardiovascular disease associated with adiponectin levels, inhibiting ADAM-17 enzyme, inhibiting a protease, treating a condition associated with TNF-alpha, and treating a condition associated with HER2-neu are disclosed. Compositions, dosage forms, and kits are also disclosed.

2 Claims, 2 Drawing Sheets

(56) References Cited

FOREIGN PATENT DOCUMENTS

| WO | WO 02/072149 | 9/2002 | | |
|---|---|---|---|---|
| WO | WO 03/023008 | 3/2003 | | |
| WO | WO 2004/022596 | 3/2004 | | |
| WO | WO 2004/061108 | 7/2004 | | |
| WO | WO 2004/063711 | 7/2004 | | |
| WO | WO2004063711 | A1 * | 7/2004 | |
| WO | WO 2004063711 | A2 * | 7/2004 | |
| WO | WO 2004/086040 | 10/2004 | | |
| WO | WO 2005/031346 | 4/2005 | | |
| WO | WO 2005/038457 | 4/2005 | | |
| WO | WO 2005/046734 | 5/2005 | | |
| WO | WO 2006/061555 | 12/2006 | | |
| WO | WO 2007/120311 | 10/2007 | | |
| WO | WO 2007120311 | A2 * | 10/2007 | ............. G01N 33/53 |
| WO | WO 2010/123720 | 10/2010 | | |

OTHER PUBLICATIONS

BLAST sequence alignment between presently claimed SEQ ID No. 5 and Pugia et al.'s SEQ ID No: 11 , 2 pages, (conducted on Oct. 3, 2013).*

BLAST sequence alignment between presently claimed SEQ ID No. 6 and Pugia et al.'s SEQ ID No. 33 , 2 pages, (conducted on Oct. 3, 2013).*

Altschul et al., "Basic Local Alignment Search Tool", J. Mol. Biol., May 15, 1990, 215, 403-410.

Baughman et al., "Release of Tumor Necrosis Factor by Alveolar Macrophages of Patients with Sarcoidosis", J. Lab. Clin. Med., Jan. 1990, 115(1), 36-42.

Bertolini et al., "Stimulation of Bone Resorption and Inhibition of Bone Formation in Vitro by Human Tumor Necrosis Factors", Nature, Feb. 1986, 319 (6), 516-518.

Bissonnette et al., "Pulmonary Inflammation and Fibrosis in a Murine Model of Asbestosis and Silicosis", Inflammation, 1989, 13(3), 329-339.

Carpino, "1-Hydroxy-7-azabenzotriazole: An Efficient Peptide Coupling Additive", J. Am. Chem. Soc., Jan. 28, 1993 115(10), 4397-4398.

Clackson et al., "Making Antibody Fragments Using Phage Display Libraries", Nature, Aug. 1991, 352, 624-628.

Cleator et al., "A Dominant Negative $Ga_s$ Mutant that Prevents Thyroid-stimulating Hormone receptor activation of cAMP Production and Inositol 1,4,5-Trisphosphate Turnover: Competition by Different G Proteins for Activation by a Common Receptor", The Journal of Biological Chemistry, Jul. 2004, 279(35), 36601-36607.

Clouse et al., "Monokine Regulation of Human Immunodeficiency Virus-1 Expression in a Chronically Infected Human T Cell Clone", The Journal of Immunology, Jan. 15, 1989, 142, 431-438.

Cohn et al., "Surrogate Markers for Cardiovascular Disease: Functional Markers", Circulation, 2004, accessed May 2, 2012, http://circ.ahajournals.org/content/109/25_suppl_1/IV-31, 109(25), Supp. 1, IV-31-IV-46.

Deen, "Metabolic Syndrome: Time for Action", American Family Physician, Jun. 15, 2004, 69(12), 2875-2882.

Dezube et al., "Pentoxifylline and Wellbeing in Patients with Cancer", The Lancet, Mar. 17, 1990, 335, p. 662.

Duh et al., "Tumor Necrosis Factor a Activates Human Immunodeficiency Virus Type 1 Through Induction of Nuclear Factor Binding to the NK kB Sites in the long Terminal Repeat", Proc. Nat. Acad. Sci., USA, Aug. 1989, 86, 5974-5978.

Elliot et al., "TNFa Blockade in Rheumatoid Arthritis: Rationale, Clinical Outcomes and Mechanisms of Action", International Society for Immunopharmacology, 1995, 17(2), 141-145.

Ferrari-Baliviera et al., "Tumor Necrosis Factor Induces Adult Respiratory Distress Syndrome in Rats", Arch Surg., Dec. 1989, 124, 1400-1405.

Folks et al., "Tumor Necrosis Factor a Induces Expression of Human Immunodeficiency Virus in a Chronically Infected T-Cell Clone", Proc. Natl. Acad. Sci., USA, Apr. 1989, 86, 2365-2368.

Gish et al., "Identification of Protein Coding Regions by database Similarity Search", Nature Genetics, Mar. 1993, 3, 266-272.

Gordon et al., "The Clinical Uses of Leptin", Current Opinion in Pharmacology, 2003, 3, 655-659.

Grau et al., "Tumor Necrosis Factor and Disease Severity in Children with Falciparum Malaria", The New England Journal of Medicine, Jun. 15, 1989, 320(24), 1586-1591.

Greenfield, "Screening for Tay-Sachs Disease", www.drspock.com/article/0.1510.6257.00.html, Aug. 27, 2004, 2 pages.

Hinshaw et al., "Survival of Primates in $LD_{100}$ Septic Shock Following Therapy with Antibody to Tumor Necrosis Factor (TNFa)", Circulatory Shock, 1990, 30, 279-292.

Hodneland, et al., "Selective Immobilization of Proteins to Self-Assembled Monolayers presenting Active Site-directed capture ligands" , Proc. Natl. Acad. Sci., Apr. 16, 2002, 99(8), 5048-5052.

Holler et al., "Increased Serum Levels of Tumor Necrosis Factor a Precede Major Complications of Bone Marrow Transplantation", Blood, Feb. 1990, 75(4), 1011-1016.

Hulme et al., "The Role of Charge Interactions in Muscarinic Agonist Binding , and receptor-response Coupling", Life Sciences, 1995, 56(11/12), 891-898.

Johnson et al., "Tumors Producing Human Tumor Necrosis Factor Induce Hypercalcemia and Osteoclastic Bone Resorption in Nude Mice", Endocrinology, 1989, 124(3), 1424-1427.

Maas et al., "Old and New Cardiovascular Risk Factors: From Unresolved Issues to New Opportunities", Atherosclerosis Supplements, 2003, 4, 5-17.

McFarlane et al., "Insulin Resistance and Cardiovascular Disease", The Journal of Clinical Endocrinology and Metabolism, Jun. 20, 2008, 86(2), 713-718.

Millar et al., "Tumor Necrosis Factor in Bronchopulmonary Secretions of Patients with Adult Respiratory Distress Syndrome", The Lancet, Sep. 23, 1989, 2, 712-714.

Monte et al., "Productive Human Immunodeficiency Virus-1 Infection of Megakaryocytic Cells is Enhanced by Tumor Necrosis Factor a", Blood, May 15, 1992, accessed May 2, 2012, http://bloodjournal.hematologylibrary.org, 79(10), 2670-2679.

Morrison et al., "Chimeric Human Antibody Molecules: Mouse antigen-binding Domains with Human Constant region domains", Proc. Natl. Acad. Sci., USA, Nov. 1984, 81, 6851-6855.

Parra et al., "Tissue Inhibitor of Metalloproteinase-1 is Increased in the Saphenofemoral Junction of Patients with Varices in the Leg", Journal of Vascular Surgery Oct. 1998, 28(4), 669-675.

Peacock, "The B-Type Natriuretic Pepetide Assay: A Rapid Test for Heart Failure", Cleveland Clinical Journal of Medicine, Mar. 2002, 69(3), 243-251.

Pignet et al., "Requirement of Tumor Necrosis factor for Development of Silica-Induced Pulmonary Fibrosis", Letters to Nature, Mar. 15, 1990, 344, 245-247.

Poli et al., "The Effect of Cytokines and Pharmacologic Agents on Chronic HIV Infection" AIDS Research and Human Retroviruses, 1992, 8(2), 191-197.

Poli et al., "Tumor Necrosis Factor a Functions in a Autocrine Manner in the Induction of Human Immunodeficiency Virus Expression", Proc. Nat. Acad. Sci., Jan. 1990, 87, 782-784.

Pugia et al., "Pathophysiology and Diagnostic Value of Urinary Trypsin Inhibitors", Clin. Chem Lab Med., 2005, 43(1), 1-16.

Shi et al., "Discovery of a Highly Selective and Efficient and Effective Reagent for Formation of Intramolecular Disulfide Bonds in Peptides", Journal of the American Chemical Society, Jul. 8, 2000, 122(12), 6809-6815.

Tietge et al., "Elevated Circulating Adiponectin Levels in Live Cirrhosis are Associated with Reduced Liver Function and altered Hepatic Hemodynamics", Am. J. Physiol. Endrocrinol. Metab., Mar. 9, 2004, 287(1), E82-E89.

Tracey et al., "Anti-Cachectin/TNF Monoclonal Antibodies Prevent Septic Shock during Lethal Bacteraemia" Letters to Nature, Dec. 23, 1987, 330(17), 662-664.

Tsuchida et al., "Nuclear Receptors as Targets for Drug Development: Molecular Mechanisms for Regulation of Obesity and Insulin

(56) References Cited

OTHER PUBLICATIONS

Resistance by Peroxisome Proliferator-Activated Receptor y CREB-Binding Protein, and Adiponectin", Journal of Pharmacological Sciences, 2005, 97, 164-170.

Van Dullemen et al., "Treatment for Crohn's Disease with Anti-Tumor Necrosis Factor Chimeric Monoclonal Antibody", Gastroenterology, Jul. 1995, 109, 129-135.

Xiao et al., "Proteomic Patterns: Their Potential for Disease Diagnosis", Molecular and Cellular Endocrinology, 2005, 230(1-2), 95-106.

Xu et al., "The Fat-Derived Hormone Adiponectin Alleviates Alcoholic and Non-Alcoholic Fatty Liver Disease in Mice", Journal of Clinical Investigation, Jul. 2003, 112(1), 91-100.

Yamauchi et al., "Adiponectin Stimulates Gluclose Utilization and Fatty-acid Oxidation by Activating AMP-Activated Protein Kinase", Nature Medicine, Nov. 2002 8(11), 1288-1295.

Yamauchi et al., "Cloning of Adiponectin Receptors that Mediate Antidiabetic Metabolic Effects", Nature, Jun. 12, 2003, 423, 762-769.

Yamauchi et al., "Globular Adiponectin Protected ob/ob Mice from Diabetes and ApoE-Deficient Mice from Atherosclerosis" The Journal of Biological Chemistry, Jan. 24, 2003, 278(4), 2461-2468.

Yamauchi et al., "The Fat-derived Hormone Adiponectin Reserves Insulin Resistance Associated with both Lipoatrophy and Obesity", Nature Medicine, Aug. 2001, 7(8), 941-946.

English Translation of Japanese Office Action of corresponding Japanese patent Application No. 2012-507255, 5 Pages.

* cited by examiner

SEQUENCE LISTING

```
<160> NUMBER OF SEQ ID NOS: 14

<210> SEQ ID NO 1
<211> LENGTH: 32
<212> TYPE: PRT
<213> ORGANISM: Artificial Sequence
<220> FEATURE:
<223> OTHER INFORMATION: Synthetic peptide

<400> SEQUENCE: 1

Val Val Ala Ala Ala Phe Val His Phe Tyr Gly Val Ser Asn Leu Gln
1               5                   10                  15

Glu Phe Arg Tyr Gly Leu Glu Gly Gly Cys Thr Asp Asp Thr Leu Leu
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: Synthetic peptide

<400> SEQUENCE: 2

Val Val Ala Gly Ala Phe Val His Phe His Gly Val Ser Asn Leu Gln
1               5                   10                  15

Glu Phe Arg Phe Met Ile Gly Gly Gly Cys Ser Glu Glu Asp Ala Leu
            20                  25                  30

<210> SEQ ID NO 3
<211> LENGTH: 2151
<212> TYPE: DNA
<213> ORGANISM: Homo sapiens
<220> FEATURE:
<221> NAME/KEY: misc_feature
<223> OTHER INFORMATION: Nucleotide sequence of ADIPOR1

<400> SEQUENCE: 3
ggcagagccc gcgaggaggt gacgcggctg cggaggtgac gcgggaggtc gcgcgcccct      60
tccggcgcgg ggagggcgct gaagatcggg gccgctcggc cgcaggccgc ctccagcgcc     120
gcgggatgta gcgcggggga ccgcggcccc cagcagagcc cgcctgcccg gcttgtctac     180
catcagaggg agatctctgc cccctggggc tgagagaccc caacctttcc ccaagctgaa     240
gctgcagggt attgaggtac cagccagatg tcttcccaca aaggatctgt ggtggcacag     300
gggaatgggg ctcctgccag taacagggaa gctgacacgg tggaactggc tgaactggga     360
```

```
cccctgctag aagagaaggg caaacgggta atcgccaacc cacccaaagc tgaagaagag    420
caaacatgcc cagtgcccca ggaagaagag gaggaggtgc gggtactgac acttcccctg    480
caagcccacc acgccatgga agatggaa gagtttgtgt acaaggtctg ggagggacgt      540
tggagggtca tcccatatga tgtgctccct gactggctaa aggacaacga ctatctgcta    600
catggtcata gacctcccat gccctccttt cgggcttgct tcaagagcat cttccgcatt    660
catacagaaa ctggcaacat ctggacccat ctgcttggtt tcgtgctgtt tctcttttg     720 ggaatcttga ccatgctcag accaaatatg tacttcatgg cccctctaca ggagaaggtg    780 gttttttggga tgttctttt gggtgcagtg ctctgcctca gcttctcctg gctctttcac    840
accgtctatt gtcattcaga gaaagtctct cggacttttt ccaaactgga ctattcaggg    900
attgctcttc taattatggg gagctttgtc ccctggctct attattcctt ctactgctcc    960
ccacagccac ggctcatcta cctctccatc gtctgtgtcc tgggcatttc tgccatcatt   1020
gtggcgcagt gggaccggtt tgccactcct aagcaccggc agacaagagc aggcgtgttc   1080
ctgggacttg gcttgagtgg cgtcgtgccc accatgcact tactatcgc tgagggcttt    1140 gtcaaggcca ccacagtggg ccagatgggc tggttcttcc tcatggctgt gatgtacatc   1200
actggagctg gcctttatgc tgctcgaatt cctgagcgct tctttcctgg aaaatttgac    1260
atatggttcc agtctcatca gattttccat gtcctggtgg tggcagcagc ctttgtccac   1320
ttctatggag tctccaacct tcaggaattc cgttacggcc tagaaggcgg ctgtactgat   1380 gacaccttc tctgagcctt cccacctgcg gggtggagga ggaacttccc aagtgctttt   1440
aaaaataact tctttgctga agtgagagga agagtctgag ttgtctgttt ctagaagaaa   1500
cctcttagag aattcagtac caaccaagct tcagcccact ttcacaccca ctgggcaata   1560
aactttccat ttccattctc ctagctgggg atggggcatg gtcaaactta gccatccct    1620 cctcagcaag gcatctaccg gcccctcaca gagacagtac tttgaaactc atgttgagat   1680
tttaccctct cctccaacca ttttgggaaa attatggact gggactcttc agaaattctg   1740
tcttttcttc tggaagaaaa tgtccctccc ttaccccat ccttaacttt gtatcctggc    1800
ttataacagg ccatccattt ttgtagcaca cttttcaaaa acaattatat accctggtcc   1860
catctttcta gggcctggat ctgcttatag agcaggaaga ataaagccac caacttttac   1920
ctagcccggc taatcatgga agtgtgtcca ggcttcaagt aacttgagtt ttaatttttt   1980
ttttttcttg gcagagtaat gtaaaattta aatgggaaaa gatatttaat atttaatact   2040
aagctttaaa aagaaacctg ctatcattgc tatgtatctt gatgcaaaga ctatgatgtt   2100
aataaaagaa agtacagaag acacttggca ttcaaaaaaa aaaaaaaaa a              2151

<210> SEQ ID NO 4
<211> LENGTH: 375
<212> TYPE: PRT
<213> ORGANISM: Homo sapiens
<220> FEATURE:
<221> NAME/KEY: misc_feature
<223> OTHER INFORMATION: Amino acid sequence of ADIPOR1

<400> SEQUENCE: 4

Met Ser Ser His Lys Gly Ser Val Val Ala Gln Gly Asn Gly Ala Pro
1               5                   10                  15

Ala Ser Asn Arg Glu Ala Asp Thr Val Glu Leu Ala Glu Leu Gly Pro
            20                  25                  30

Leu Leu Glu Glu Lys Gly Lys Arg Val Ile Ala Asn Pro Pro Lys Ala
        35                  40                  45
```

```
Glu Glu Glu Gln Thr Cys Pro Val Pro Gln Glu Glu Glu Glu Val
 50                  55                  60

Arg Val Leu Thr Leu Pro Leu Gln Ala His His Ala Met Glu Lys Met
 65                  70                  75                  80

Glu Glu Phe Val Tyr Lys Val Trp Glu Gly Arg Trp Arg Val Ile Pro
                 85                  90                  95

Tyr Asp Val Leu Pro Asp Trp Leu Lys Asp Asn Asp Tyr Leu Leu His
                100                 105                 110

Gly His Arg Pro Pro Met Pro Ser Phe Arg Ala Cys Phe Lys Ser Ile
                115                 120                 125

Phe Arg Ile His Thr Glu Thr Gly Asn Ile Trp Thr His Leu Leu Gly
            130                 135                 140

Phe Val Leu Phe Leu Phe Leu Gly Ile Leu Thr Met Leu Arg Pro Asn
145                 150                 155                 160

Met Tyr Phe Met Ala Pro Leu Gln Glu Lys Val Val Phe Gly Met Phe
                165                 170                 175

Phe Leu Gly Ala Val Leu Cys Leu Ser Phe Ser Trp Leu Phe His Thr
                180                 185                 190

Val Tyr Cys His Ser Glu Lys Val Ser Arg Thr Phe Ser Lys Leu Asp
                195                 200                 205

Tyr Ser Gly Ile Ala Leu Leu Ile Met Gly Ser Phe Val Pro Trp Leu
                210                 215                 220

Tyr Tyr Ser Phe Tyr Cys Ser Pro Gln Pro Arg Leu Ile Tyr Leu Ser
225                 230                 235                 240

Ile Val Cys Val Leu Gly Ile Ser Ala Ile Ile Val Ala Gln Trp Asp
                245                 250                 255

Arg Phe Ala Thr Pro Lys His Arg Gln Thr Arg Ala Gly Val Phe Leu
                260                 265                 270

Gly Leu Gly Leu Ser Gly Val Val Pro Thr Met His Phe Thr Ile Ala
            275                 280                 285

Glu Gly Phe Val Lys Ala Thr Thr Val Gly Gln Met Gly Trp Phe Phe
            290                 295                 300

Leu Met Ala Val Met Tyr Ile Thr Gly Ala Gly Leu Tyr Ala Ala Arg
305                 310                 315                 320

Ile Pro Glu Arg Phe Phe Pro Gly Lys Phe Asp Ile Trp Phe Gln Ser
                325                 330                 335

His Gln Ile Phe His Val Leu Val Ala Ala Ala Phe Val His Phe
                340                 345                 350

Tyr Gly Val Ser Asn Leu Gln Glu Phe Arg Tyr Gly Leu Glu Gly Gly
            355                 360                 365

Cys Thr Asp Asp Thr Leu Leu
            370                 375

<210> SEQ ID NO 5
<211> LENGTH: 25
<212> TYPE: PRT
<213> ORGANISM: Artificial Sequence
<220> FEATURE:
<223> OTHER INFORMATION: Synthetic peptide

<400> SEQUENCE: 5

His Phe Tyr Gly Val Ser Asn Leu Gln Glu Phe Arg Tyr Gly Leu Glu
1               5                   10                  15

Gly Gly Cys Thr Asp Asp Thr Leu Leu
            20                  25
```

<210> SEQ ID NO 6
<211> LENGTH: 25
<212> TYPE: PRT
<213> ORGANISM: Artificial Sequence
<220> FEATURE:
<223> OTHER INFORMATION: Synthetic peptide

<400> SEQUENCE: 6

His Phe His Gly Val Ser Asn Leu Gln Glu Phe Arg Phe Met Ile Gly
1               5                   10                  15

Gly Gly Cys Ser Glu Glu Asp Ala Leu
            20                  25

<210> SEQ ID NO 7
<211> LENGTH: 18
<212> TYPE: PRT
<213> ORGANISM: Artificial Sequence
<220> FEATURE:
<223> OTHER INFORMATION: Synthetic peptide

<400> SEQUENCE: 7

Leu Gln Glu Phe Arg Tyr Gly Leu Glu Gly Gly Cys Thr Asp Asp Thr
1               5                   10                  15

Leu Leu

<210> SEQ ID NO 8
<211> LENGTH: 18
<212> TYPE: PRT
<213> ORGANISM: Artificial Sequence
<220> FEATURE:
<223> OTHER INFORMATION: Synthetic peptide

<400> SEQUENCE: 8

Leu Gln Glu Phe Arg Phe Met Ile Gly Gly Gly Cys Ser Glu Glu Asp
1               5                   10                  15

Ala Leu

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Gly Gly Cys Thr Asp Asp Thr Leu Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Gly Gly Cys Ser Glu Glu Asp Ala Leu
1               5

<210> SEQ ID NO 11
<211> LENGTH: 30
<212> TYPE: PRT
<213> ORGANISM: Artificial Sequence
<220> FEATURE:

```
<223> OTHER INFORMATION: Synthetic peptide

<400> SEQUENCE: 11

His Val Leu Val Val Ala Ala Ala Phe Val His Phe Tyr Gly Val Ser
1               5                   10                  15

Asn Leu Gln Glu Phe Arg Tyr Gly Leu Glu Gly Gly Cys Thr
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Synthetic peptide

<400> SEQUENCE: 12

His Ile Phe Val Val Ala Gly Ala Phe Val His Phe His Gly Val Ser
1               5                   10                  15

Asn Leu Gln Glu Phe Arg Phe Met Ile Gly Gly Gly Cys Ser
            20                  25                  30

<210> SEQ ID NO 13
<211> LENGTH: 34
<212> TYPE: PRT
<213> ORGANISM: Artificial Sequence
<220> FEATURE:
<223> OTHER INFORMATION: Synthetic peptide

<400> SEQUENCE: 13

His Phe His Gly Val Ser Asn Leu Gln Glu Phe Arg Phe Met Ile Gly
1               5                   10                  15

Gly Gly Cys Ser Glu Glu Asp Ala His Val Leu Val Val Ala Ala Ala
            20                  25                  30

Phe Val

<210> SEQ ID NO 14
<211> LENGTH: 34
<212> TYPE: PRT
<213> ORGANISM: Artificial Sequence
<220> FEATURE:
<223> OTHER INFORMATION: Synthetic peptide

<400> SEQUENCE: 14

His Phe Tyr Gly Val Ser Asn Leu Gln Glu Phe Arg Tyr Gly Leu Glu
1               5                   10                  15

Gly Gly Cys Thr Asp Asp Thr Leu His Ile Phe Val Val Ala Gly Ala
            20                  25                  30

Phe Val
```

US 8,865,648 B2

MONOMERIC AND DIMERIC FORMS OF ADIPONECTIN RECEPTOR FRAGMENTS AND METHODS OF USE

CROSS REFERENCE TO RELATED APPLICATIONS

This application is the national stage of International Appl. No. PCT/US10/30836, filed Apr. 13, 2010, which claims the benefit of U.S. application Ser. No. 61/171,979, filed Apr. 23, 2009. This application is also related to:
U.S. application Ser. No. 10/572,882, which is the national stage entry of PCT/EP04/10383 filed Sep. 16, 2004;
U.S. application Ser. No. 10/572,883, which is the national stage entry of PCT/EP04/10384 filed Sep. 16, 2004;
U.S. application Ser. No. 60/748,305 filed Dec. 7, 2005;
WO 2007/120,311 filed Dec. 4, 2006;
U.S. Application No. 60/991,328 filed Nov. 30, 2007; and
U.S. application Ser. No. 12/169,983 filed Jul. 9, 2008;
the entire disclosures of which are incorporated herein by reference.

FIELD OF THE INVENTION

The present invention generally relates to adiponectin receptor fragments. More particularly, the invention relates to monomeric and dimeric forms of adiponectin receptor fragments, to methods of using the monomeric and dimeric forms of the adiponectin receptor fragments diagnostically and therapeutically, and to compositions, dosage forms, and kits comprising the monomeric and dimeric forms of the adiponectin receptor fragments.

BACKGROUND OF THE INVENTION

Adiponectin Receptor 1 (ADIPOR1) is a seven transmembrane G protein coupled receptor (GPCR). See, for example, WO 01/012662 and WO 01/090304. Many medically significant biological processes are mediated by signal transduction pathways that involve G-proteins [Lefkowitz, Nature 351, 353-354 (1991)]. Certain extra cellular messengers (ECM) or C-terminal fragments (CTF), which are peptide fragments from the C-terminal of ADIPOR1 (R1 CTF) and ADIPOR2 (R2 CTF), have diagnostic value in human blood. Their usefulness was confirmed using a polyclonal antibody with a mass measuring SELDI-TOF immuno-affinity method. Those inventions are the subject of related application WO 2007/120,311, which is incorporated herein by reference. In that work, a particular long peptide sequence of 32 amino acids of R1 CTF was identified that was completely absent from all diabetic patients tested. Shorter peptide sequences were also found in blood but in both healthy and diabetic patients. The levels of the shorter peptide sequences were generally increased with disease state.

It was also previously discovered that monomeric ECM32 (SEQ ID NO:1) (R1 CTF32), a fragment of 3473 Da as confirmed by two separate monoclonal antibodies, when administered to patients, acted as an insulin-sensitizing agent. That invention is the subject of copending application U.S. Ser. No. 12/169,983 filed Jul. 9, 2008. As such, this C-terminal fragment of ADIPOR1 may be a useful therapeutic agent to increase insulin secretion in patients in need thereof, including, but not limited to, patients suffering from diabetes, abnormal adipocyte activity, and insulin resistance.

It has now been discovered that the dimeric forms of ECM32 and dimeric forms of ECM25 are biologically active. It has also been discovered that heterodimeric form of ECM32, or R1 CTF32 R2 CTF32 (SEQ ID NO:1 linked via a disulfide bond to SEQ ID NO:2), is more active than homodimeric forms of ECM32 (R1 CTF32 R1 CTF32) (SEQ ID NO:1 linked via a disulfide bond to SEQ ID NO:1 or SEQ ID NO:2 linked via a disulfide bond to SEQ ID NO:2)). The methods, compositions, dosage forms, and kits of the present invention are directed toward these, as well as other, important ends.

SUMMARY OF THE INVENTION

It is has been unexpectedly discovered that certain dimeric forms of C-terminal fragments of ADIPOR1 inhibit the enzymatic activity of ADAM-17 and insulin degradation enzyme (IDE) and thereby impact insulin levels and signal peptides impacted by these enzyme such as TNF-α. Accordingly, these dimeric forms of C-terminal fragments are useful in therapeutic methods of treating diabetes, abnormal adipocyte activity, and insulin resistance. Determining the level of the dimeric forms of the C-terminal fragments may be used diagnostically. Useful compositions, dosage forms, and kits have also been discovered.

The present invention is directed, in part, to methods for determining progression of a condition, onset of a condition, or efficacy of treatment of a condition characterized by an adipocyte imbalance in a patient, comprising:
determining a level of a peptide in a biological fluid sample obtained from said patient;
wherein said peptide is selected from the group consisting of:
  a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
  a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
  a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
  a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
  a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
  a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;

a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;

a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;

a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer; and correlating the level with said progression of a condition, onset of a condition, or efficacy of treatment of a condition characterized by an adipocyte imbalance.

The present invention is also directed, in part, to methods of treating diabetes in a patient in need thereof, comprising the step of:

administering to said patient an effective amount of a peptide or a pharmaceutically-acceptable salt thereof;

wherein said peptide is selected from the group consisting of:

a monomeric peptide having at least about 75% identity with SEQ ID NO:2;

a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;

a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;

a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;

a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;

a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;

a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;

a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;

a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;

a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In other embodiments, the invention is directed to methods of treating abnormal adipocyte activity in a patient in need thereof, comprising the step of:

administering to said patient an effective amount of a peptide or a pharmaceutically-acceptable salt thereof;

wherein said peptide is selected from the group consisting of:

a monomeric peptide having at least about 75% identity with SEQ ID NO:2;

a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;

a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;
a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;
a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;
a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;
a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In another embodiment, the invention is directed to methods of treating insulin resistance in a patient in need thereof, comprising the step of:
administering to said patient an effective amount of a peptide or a pharmaceutically-acceptable salt thereof;
wherein said peptide is selected from the group consisting of:
a monomeric peptide having at least about 75% identity with SEQ ID NO:2;
a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;
a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;
a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;
a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;
a dimer of said first heterodimer;
a dimer of said first homodimer;
a dimer of said second homodimer;

a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In yet other embodiments, the invention is directed to methods of treating metabolic syndrome in a patient in need thereof; comprising the step of:
administering to said patient an effective amount of a peptide or a pharmaceutically-acceptable salt thereof;
wherein said peptide is selected from the group consisting of:
a monomeric peptide having at least about 75% identity with SEQ ID NO:2;
a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;
a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;
a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;
a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;
a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In yet other embodiments, the invention is directed to methods of inhibiting insulin degradation enzyme (IDE) in a patient, comprising the step of:
administering to said patient an effective amount of a peptide or a pharmaceutically-acceptable salt thereof;
wherein said peptide is selected from the group consisting of:
a monomeric peptide having at least about 75% identity with SEQ ID NO:2;
a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;

a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;

a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In other embodiments, the invention is directed to methods of treating Alzheimer's disease in a patient, comprising the step of:

administering to said patient an effective amount of a peptide or a pharmaceutically-acceptable salt thereof;

wherein said peptide is selected from the group consisting of:

a monomeric peptide having at least about 75% identity with SEQ ID NO:2;

a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;

a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;

a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;

a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;

a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;

a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;

a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;

a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;

a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In other embodiments, the invention is directed to methods of treating cardiovascular disease associated with adiponectin levels in a patient, comprising the step of:

administering to said patient an effective amount of a peptide or a pharmaceutically-acceptable salt thereof;

wherein said peptide is selected from the group consisting of:

a monomeric peptide having at least about 75% identity with SEQ ID NO:2;

a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;

a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;

a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;
a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;
a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;
a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;
a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In yet other embodiments, the invention is directed to methods of inhibiting ADAM-17 enzyme in a patient, comprising the step of:
administering to said patient an effective amount of a peptide or a pharmaceutically-acceptable salt thereof;
wherein said peptide is selected from the group consisting of:
a monomeric peptide having at least about 75% identity with SEQ ID NO:2;
a first heterodimer comprising a first mer unit and a second mer unit, wherein said first mer unit has at least about 75% identity with SEQ ID NO:1 and wherein second mer unit has at least about 75% identity with SEQ ID NO:2, and wherein said first mer unit and said second mer unit are linked via a disulfide bond;
a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;
a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;
a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;
a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;
a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

Thus, the peptides of the invention are useful as an anti-TNF alpha therapy and as an anti-HER2 neu therapy. Anti-TNF alpha therapy is important in treating inflammation and autoimmune diseases, such as lupus, rheumatoid arthritis, and type-1 diabetes. Anti-HER2 neu therapy is important in impacting tumor growth, especially in breast cancer.

In yet other embodiments, the invention is directed to methods of treating a condition associated with TNF-alpha in a patient, comprising the step of:
  administering to said patient an effective amount of a peptide or a pharmaceutically-acceptable salt thereof;
  wherein said peptide is selected from the group consisting of:
    a monomeric peptide having at least about 75% identity with SEQ ID NO:2;
    a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
    a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
    a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
    a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
    a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
    a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
    a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;
    a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;
    a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;
    a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;
    a dimer of said first heterodimer;
    a dimer of said first homodimer;
    a dimer of said second homodimer;
    a dimer of said second heterodimer;
    a dimer of said third homodimer;
    a dimer of said fourth homodimer;
    a dimer of said third heterodimer;
    a dimer of said fourth heterodimer;
    a dimer of said fifth heterodimer; and
    a dimer of said sixth heterodimer.

In yet other embodiments, the invention is directed to methods of treating a condition associated with HER2 neu in a patient, comprising the step of:
  administering to said patient an effective amount of a peptide or a pharmaceutically-acceptable salt thereof;
  wherein said peptide is selected from the group consisting of:
    a monomeric peptide having at least about 75% identity with SEQ ID NO:2;
    a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
    a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
    a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
    a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
    a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
    a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
    a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;
a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;
a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;
a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;
a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In yet other embodiments, the invention is directed to methods of inhibiting a protease in a patient, comprising:
administering to said patient an effective amount of a peptide or a pharmaceutically-acceptable salt thereof;
wherein said peptide is selected from the group consisting of:
a monomeric peptide having at least about 75% identity with SEQ ID NO:1;
a monomeric peptide having at least about 75% identity with SEQ ID NO:2;
a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
a third homodimer comprising a first mer unit and a second mer unit, wherein said first mer unit has at least about 75% identity with SEQ ID NO:5 and wherein second mer unit has at least about 75% identity with SEQ ID NO:5, and wherein said first mer unit and said second mer unit are linked via a disulfide bond;
a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;
a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;
a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;
a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;
a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer; and
wherein said protease is insulysin/insulin degradation enzyme (IDE), ADAM-17 peptidase, omptin, aureolysin, falcilysin, pepsin A, pepsin B, cathespsin D, cathespsin E, cathespsin G, cathespsin H, cathespsin L, acrocylindropepsin, acid peptidase (*Cladosporium*), rhodotorulapepsin, grifolisin, physarolisin, peptidase K, subtilisin aprM, subtilisin BPN', high alkaline protease, M-peptidase sp. KSM-K16, subtilisin Carlsberg, meprinpeptidase, streptogrisin B, chymotrypsin C, peptidase Ci, camelysis, deuterolysin, aminopeptidase Ap1, endothelin-converting enzyme 1, neprilysin, leucolysisn, presenilin, thermopsin, retropepsin (human Tcell leukemia virus), bovine immunodeficiency virus retropepsin, candidapepsin SAP2, candidapepsin SAP3, candidapepsin SAP6, candiparapsin SAP1, or rhizopuspepsin, provided that said protease is not IDE or ADAM-17 peptidase when said peptide is a monomeric peptide having at least about 75% identity with SEQ ID NO:1.

In yet other embodiments, the invention is directed to methods of treating insulin resistance in a patient in need thereof, comprising the step of:
administering to said patient an effective amount of a peptide or a pharmaceutically-acceptable salt thereof;

wherein said peptide is selected from the group consisting of:
- a monomeric peptide having at least about 75% identity with SEQ ID NO:2;
- a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
- a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
- a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
- a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
- a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
- a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
- a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;
- a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;
- a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;
- a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;
- a dimer of said first heterodimer;
- a dimer of said first homodimer;
- a dimer of said second homodimer;
- a dimer of said second heterodimer;
- a dimer of said third homodimer;
- a dimer of said fourth homodimer;
- a dimer of said third heterodimer;
- a dimer of said fourth heterodimer;
- a dimer of said fifth heterodimer; and
- a dimer of said sixth heterodimer.

In yet other embodiments, the invention is directed to methods of causing insulin secretion in a patient, comprising the step of:
administering to said patient an effective amount of a peptide or a pharmaceutically-acceptable salt thereof;
wherein said peptide is selected from the group consisting of:
- a monomeric peptide having at least about 75% identity with SEQ ID NO:2;
- a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
- a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
- a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
- a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
- a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
- a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
- a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;
- a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;
- a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;
a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;
a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In yet other embodiments, the invention is directed to methods of increasing insulin level in a patient, wherein said patient does not suffer from diabetes, comprising the step of:
administering to said patient an effective amount of a peptide or a pharmaceutically-acceptable salt thereof;
wherein said peptide is selected from the group consisting of:
a monomeric peptide having at least about 75% identity with SEQ ID NO:2;
a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
a third heterodimer comprising a first mer unit and a second mer unit, wherein said first mer unit has at least about 75% identity with SEQ ID NO:1 and wherein second mer unit has at least about 75% identity with SEQ ID NO:5, and wherein said first mer unit and said second mer unit are linked via a disulfide bond;
a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;
a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;
a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;
a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In another embodiment, the invention is directed to compositions, comprising:
a peptide or a pharmaceutically-acceptable salt thereof;
wherein said peptide is selected from the group consisting of:
a monomeric peptide having at least about 75% identity with SEQ ID NO:2;
a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;

a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;

a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;

a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;

a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer; and
at least one pharmaceutically-acceptable carrier.

In further embodiments, the invention is directed to compositions, comprising:

a purified peptide or a pharmaceutically-acceptable salt thereof;

wherein said peptide is selected from the group consisting of:

a monomeric peptide having at least about 75% identity with SEQ ID NO:2;

a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;

a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;

a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;

a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;

a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;

a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;

a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;

a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;

a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer; and optionally, at least one pharmaceutically-acceptable carrier.

In yet other embodiments, the invention is directed to injectable dosage forms, comprising:
the composition described herein; and
at least one solvent for said peptide.

In other embodiments, the invention is directed to inhalable dosage forms, comprising:
the composition described herein; and
at least one pharmaceutically-acceptable carrier for administration of said peptide via inhalation.

In another embodiment, the invention is directed to kits, comprising:

instructions for administering an injectable dosage form to a patient;

a container comprising a composition described herein;

a container comprising a pharmaceutically-acceptable solvent for said compositions.

In other embodiments, the invention is directed to kits, comprising:

instructions for administering an inhalable dosage form to a patient;

a container comprising a composition described herein;

a container comprising a pharmaceutically-acceptable solvent for said composition.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

Figure 1:
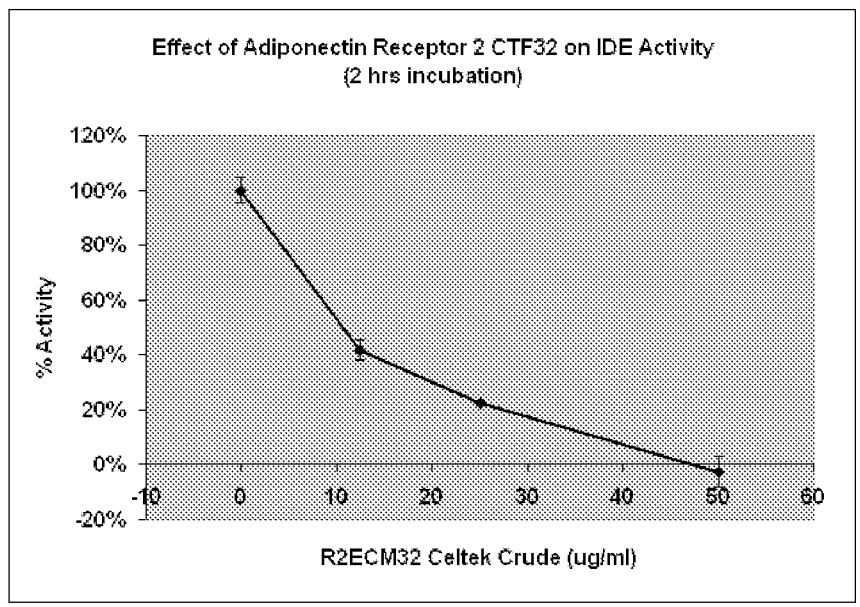
FIG. 1 is a plot of IDE activity as a function of the level of R2 CTF32 (SEQ ID NO:2) with a two hour incubation.

As employed above and throughout the disclosure, the following terms, unless otherwise indicated, shall be understood to have the following meanings As used herein, the singular forms "a," "an," and "the" include the plural reference unless the context clearly indicates otherwise.

As used herein, the term "about," when referring to a measurable value such as an amount, a temporal duration, and the like, is meant to encompass variations of ±20%, preferably ±10%, more preferably ±5%, even more preferably ±1%, and yet even more preferably ±0.1% from the specified value, as such variations are appropriate to perform the disclosed methods and compositions.

As used herein, "effective amount" refers to an amount of the active ingredient as described herein that may be effective to prevent, reduce or eliminate the symptoms or condition and, with respect to this invention, including to treat diabetes and any other conditions disclosed herein that are associated with adiponectin levels, TNF-alpha, HER2 neu, to treat abnormal adipocyte activity, to treat metabolic syndrome, to cause insulin secretion, to increase insulin levels, to inhibit insulin degradation enzyme, to treat Alzheimer's disease, to treat cardiovascular disease associated with adiponectin levels, to inhibit ADAM-17 enzyme, to treat a condition associated with TNF-alpha, and to treat a condition associated with HER2 neu. In general, the effective amount of the ADIPO R1 fragments of the invention, ranges from about 0.25 mg per kg patient weight to about 200 mg per kg patient weight, preferably about 25 mg per kg patient weight to about 175 mg per kg patient weight, and more preferably about 30 mg per kg patient weight to about 150 mg per kg patient weight (and all combinations and subcombinations therein).

As used herein, "treating" refers to the preventative, curative, and palliative treatment of a condition, and minimally requires a palliative effect.

As used herein, "pharmaceutically-acceptable" refers to those compounds, materials, compositions, and/or dosage forms that are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically-acceptable salts" refer to derivatives of the disclosed compounds wherein the parent compound is modified by making acid or base salts thereof, including acid addition salts and base addition salts. Examples of pharmaceutically-acceptable salts include, but are not limited to, mineral or organic acid salts of basic residues such as amines; alkali or organic salts of acidic residues such as carboxylic acids; and the like. The term "acid addition salt" refers to the corresponding salt derivative of a parent compound that has been prepared by the addition of an acid. The pharmaceutically-acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, adipic, alginic, aspartic, hydroxymaleic, phenylacetic, glutamic, benzoic, salicylic, sulfanilic, 2-acetoxybenzoic, fumaric, benzenesulfonic, toluenesulfonic, methanesulfonic, 2-napthalenesulfonic, ethane disulfonic, oxalic, isethionic, glucoheptanoic, glycerophosphoric, hemisulfanic, heptanoic, hexanoic, hydrochloric, hydrobromic, hydroiodic, 2-hydroxyethanesulfonic, 2-napthalenesulfonic, pectinic, phosphoric, sulfuric, 3-phenylpropionic, picric, pivalic, thiocyanic, p-toluenesulfonic, butyric, camphoric, camphorsulfonic, digluconic, cyclopentanepropionic, bisulfuric, dodecylsulfuric, ethanesulfonic, and undecanoic and the like.

Thus, the term "base addition salt" refers to the corresponding salt derivative of a parent compound that has been prepared by the addition of a base. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. The pharmaceutically-acceptable salts include the conventional salts or the quaternary ammonium salts of the parent compound formed, for example, from inorganic or organic bases. For example, such conventional salts include, but are not limited to, those derived from inorganic bases such as lithium hydroxide, sodium hydroxide, potassium hydroxide, calcium hydroxide, magnesium hydroxide and ammonium hydroxide and the salts prepared from organic amines, such as methyl amine, ethyl amine, isopropyl amine, piperidine, piperizine, pyrrolidine, ethanolamine, morpholine, diazapine, ethylene diamine, pyridine, quinoline, quinuclidine, and the like.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, "dosage unit" refers to physically discrete units suited as unitary dosages for the particular patient to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

As used herein, "patient" refers to an animal, including a mammal, preferably a human.

As used herein, "healthy" refers to a patient that is not currently suffering from a condition or disease and includes a patient who is predisposed to suffering a condition. For example, a pre-diabetic patient would be considered a healthy patient for the purposes of this invention.

As used herein, "polypeptide," "peptide," and "protein fragment" are used interchangeably herein to refer to a polymer of amino acid residues. The terms includes amino acid polymers in which one or more amino acid residues is an artificial chemical mimetic of a corresponding naturally-occurring amino acid, as well as to naturally-occurring amino acid polymers and non-naturally-occurring amino acid polymers.

As used herein, "polynucleotide" means a polymeric form of nucleotides of at least about 10 bases or base pairs in length, either ribonucleotides or deoxyribonucleotides or a modified form thereof.

As used herein, "percent identity" refers the proportion of the polypeptide sequence that matches the reference polypeptide sequence and can be determined by comparing two optimally aligned sequences over a comparison window, wherein the polypeptide sequence in the comparison window can comprise additions, deletions (i.e., gaps), derivatization, and/or conservative amino acid substitutions as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison, and multiplying the result by 100 to yield the percentage of sequence identity. Identity is evaluated using any of the variety of sequence comparison algorithms and programs known in the art. Such algorithms and programs include, but are by no means limited to, TBLASTN, BLASTP, FASTA, TFASTA, CLUSTALW, FASTDB, the entire disclosures of which are incorporated herein by reference. See, also, Pearson, et al., Proc. Natl. Acad. Sci. U.S.A., 85:2444-2448, 1988; Atlschul, et al., *J. Mol. Biol.*, 215:403410, 1990; Thompson, et al., *Nucleic Acids Res.*, 22:4673-4680, 1994; Higgins, et al., *Meth. Enzymol.*, 266:383402, 1996; Altschul, et al., *Nature Genetics*, 3:266-272, 1993; Brutlag, et al., *Comp. App. Biosci.*, 6:237-44, 1990.

As used herein, "derivatization" refers to the process of chemically modifying by techniques such as ubiquitination, labeling, peglyation (i.e., derivatization with polyethylene glycol), and chemical insertion or substitution of amino acids, such as ornithine, which do not normally occur in human proteins.

As used herein, "conservative amino acid substitution" refers to the replacement of one amino acid with another having similar structure and/or chemical properties, such as the replacement of a leucine with an isoleucine or valine, an aspartate with a glutamate, or a threonine with a serine.

As used herein, "TACE" refers to tumor necrosis factor α-converting enzyme, and may be used interchangeably with "ADAM-17," which refers to disintegrin and metalloprotease domain 17, an enzyme that cleaves TNF and HERn.

As used herein, "diabetes" refers to diabetes mellitus, a chronic hyperglycemia due to defective insulin secretion and/or action. The World Health Organization recognizes three main forms of diabetes mellitus: type I, type II, and gestational diabetes. While all forms are due to the beta cells of the pancreas being unable to produce sufficient insulin to prevent hyperglycemia, the causes are different. Type I diabetes is usually due to autoimmune destruction of the pancreatic beta cells. Type II diabetes is characterized by insulin resistance in target tissues, which creates a need for abnormally high amounts of insulin and diabetes develops when the beta cells cannot meet this demand. Gestational diabetes is similar to type II diabetes in that it involves insulin resistance; the hormones of pregnancy can cause insulin resistance in women genetically predisposed to developing this condition. Gestational diabetes typically resolves with delivery of the child, however types I and II diabetes are chronic conditions. All types are treatable with insulin. Type I diabetes, in which insulin is not secreted by the pancreas, is directly treatable only with injected or inhaled insulin, although dietary and other lifestyle adjustments are part of management. Type II may be managed with a combination of dietary treatment, tablets and injections and, frequently, insulin supplementation.

Normal insulin sensitivity results when insulin cause fat cells to produce adiponectin. Adiponectin interacts with the adiponectin receptor 2 in the liver and the adiponectin receptor 1 in the muscle to stop glucose production and cause glycolysis and fatty acid oxidation. The adiponectin receptor 1 reacts with a cleaved form of adiponectin called globular adiponectin whereas adiponectin receptor 2 reacts to full length adiponectin.

Insulin resistance occurs when adipocytes become hypertropic and produce less adiponectin in response to insulin. In this state, the cells become more apoptotic and cell division slows. As a result, plasma adiponectin levels decrease. Insulin levels rise in an effort to cause cells to release more adiponectin. However, as the insulin resistance worsens more insulin and less adiponectin is produced. The lower level of adiponectin results in less glycolysis and fatty acid oxidation in muscle and prevents liver glucose production from stopping. As used herein, "insulin resistance" refers to a decrease in an individual in the biological action of insulin in vivo as assessed by the rate of disposal of glucose from the bloodstream (e.g., into insulin-sensitive tissue, such as muscle, fat, and liver).

As used herein, "metabolic syndrome" or "syndrome X" refers to a cluster of risk factors that is blamed for the excess cardiovascular disease morbidity among overweight and obese patients and patients with type II diabetes mellitus. Both the World Health Organization and National Cholesterol Education Program—Adult Treatment Patent (NCEP-ATP III) have set forth diagnostic criteria for metabolic syndrome (Darwin Deen, *American Family Physician*, 69 (12): 2875-2882 (2004):

TABLE 1

Diagnostic Criteria for Metabolic Syndrome According to the WHO and the ATP III

| Component | WHO diagnostic criteria (insulin resistance* plus two of the following) | ATP III diagnostic criteria (three of the following) |
|---|---|---|
| Abdominal/central obesity | Waist to hip ratio: >0.90 (men), >0.85 (women), or BMI >30 kg per m² | Waist circumference: >102 cm (40 in) in men, >88 cm (35 in) in women |
| Hypertriglyceridemia | >=150 mg per dL (>=1.7 mmol per L) | >=150 mg per dL |
| Low HDL cholesterol | <35 mg per dL (<0.9 mmol per L) for men, <39 mg per dL (<1.0 mmol per L) for women | <40 mg per dL (<1.036 mmol per L) for men, <50 mg per dL (<1.295 mmol per L) for women |
| High blood pressure | >=140/90 mm Hg or documented use of antihypertensive therapy | >=130/85 mm Hg or documented use of antihypertensive therapy |
| High fasting glucose | Impaired glucose tolerance, impaired fasting glucose, insulin resistance, or diabetes | >=110 mg per dL (>=6.1 mmol per L)† |
| Microalbuminuria | Urinary albumin to creatinine ratio: 30 mg per g, or albumin excretion rate: 20 mcg per minute | |

WHO = World Health Organization; ATP = Adult Treatment Panel; BMI = body mass index; HDL = high-density lipoprotein.
*Insulin resistance is identified by type 2 diabetes mellitus or impaired fasting glucose.

As used herein, "cardiovascular disease" refers to any disease that affects the heart and blood vessels, including diseases related to atherosclerosis (arterial disease) that can cause heart attacks and certain types of strokes and specifically including, but not limited to, cardiovascular disease is congestive heart failure, acute myocardial infarction, coronary artery disease, vascular blockage, arteriosclerosis, atherosclerosis, ischemia, and combinations thereof.

As used herein, "condition associated with TNF-alpha" refers to any pathological condition or disease mediated by TNF-alpha converting enzyme (TACE) in a mammal. Examples of such conditions and diseases include, but are not limited to: HIV; hepatitis; adult respiratory distress syndrome; bone-resorption diseases; chronic obstructive pulmonary diseases; chronic pulmonary inflammatory diseases; dermatitis; cystic fibrosis; septic shock; sepsis; endotoxic shock; hemodynamic shock; sepsis syndrome; post ischemic reperfusion injury; meningitis; psoriasis; fibrotic disease; cachexia; graft versus host disease (GVHD); graft rejection; auto-immune disease; rheumatoid spondylitis; arthritic conditions, such as rheumatoid arthritis, rheumatoid spondylitis and osteoarthritis; osteoporosis; inflammatory-bowel disease; Crohn's disease; ulcerative colitis; multiple sclerosis; systemic lupus erythematosus; ENL in leprosy; radiation damage; asthma; type-1 diabetes, and hyperoxic alveolar injury, and combinations thereof. Tracey, et al., 1987, *Nature* 330:662 664 and Hinshaw, et al., 1990, *Circ. Shock* 30:279 292 (endotoxic shock); Dezube, et al., 1990, *Lancet*, 335:662 (cachexia); Millar, et al., 1989, *Lancet* 2:712 714 and Ferrai-Baliviera, et al., 1989, *Arch. Surg.* 124:1400 1405 (adult respiratory distress syndrome); Bertolini, et al., 1986, *Nature* 319:516 518, Johnson, et al., 1989, *Endocrinology* 124:1424 1427, Holler, et al., 1990, *Blood* 75:1011 1016, and Grau, et al., 1989, *N. Engl. J. Med.* 320:1586 1591 (bone resorption diseases); Pignet, et al., 1990, *Nature,* 344:245 247, Bissonnette, et al., 1989, *Inflammation* 13:329 339 and Baughman, et al., 1990, *J. Lab. Clin. Med.* 115:36 42 (chronic pulmonary inflammatory diseases); Elliot, et al., 1995, *Int. J. Pharmac.* 17:141 145 (rheumatoid arthritis); von Dullemen, et al., 1995, *Gastroenterology,* 109:129 135 (Crohn's disease); Duh, et al., 1989, *Proc. Nat. Acad. Sci.* 86:5974 5978, Poll, et al., 1990, *Proc. Nat. Acad. Sci.* 87:782 785, Monto, et al., 1990, *Blood* 79:2670, Clouse, et al., 1989, *J. Immunol.* 142, 431 438, Poll, et al., 1992, *AIDS Res. Hum. Retrovirus,* 191 197, Poll, et al. 1990, *Proc. Natl. Acad. Sci.* 87:782 784, Folks, et al., 1989, *PNAS* 86:2365 2368 (HIV and opportunistic infections resulting from HIV).

As used herein, "condition associated with HER2-neu" refers to any pathological condition or disease mediated by human epidermal growth factor receptor 2 (HER2-neu) in a mammal, including tumor growth, especially in breast cancer.

The nucleotide sequence of ADIPOR1 is accessible in public databases by the accession number NM_015999 and is given in SEQ ID NO:3. The amino acid sequence of ADIPOR1 is depicted in SEQ ID NO:4. The adiponectin receptors, ADIPOR1 and ADIPOR2, serve as receptors for globular and full-length adiponectin and mediate increased AMPK and PPAR-alpha ligand activities, as well as fatty acid oxidation and glucose uptake by adiponectin [Yamauchi, et al., *Nature* 423: 762-769 (2003)]. Yamauchi, et al. [Yamauchi, et al., *Nature* 423: 762-769 (2003)] isolated cDNAs encoding ADIPOR1 and ADIPOR2 by expression cloning. The receptor ADIPOR1 is published in [Yamauchi, et al., *Nature* 423: 762-769 (2003)].

The monomeric, homodimeric, and heterodimeric forms of the C-terminal fragments of ADIPOR1 and ADIPOR2 may be used diagnostically and therapeutically.

In one aspect, the invention is directed to methods for determining progression of a condition, onset of a condition, or efficacy of treatment of a condition characterized by an adipocyte imbalance in a patient, comprising:

determining a level of a peptide in a biological fluid sample obtained from said patient;

wherein said peptide is selected from the group consisting of:

a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;

a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;

a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;

a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;

a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;

a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;

a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;

a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;

a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer; and
correlating the level with said progression of a condition, onset of a condition, or efficacy of treatment of a condition characterized by an adipocyte imbalance.

In a preferred embodiment, the level of peptide is determined using an immunoassay, especially an ELISA assay. In certain preferred embodiments, polyclonal and monoclonal antibodies, which are specific for either the R1 CTF or R2 CTF, are employed. The following antigen sequences may be used to raise antibodies that are specific in detecting either R1 CTF or R2 CTF without cross reactivity:

```
(R1 CTF9):
                                        SEQ ID NO: 9
GGCTDDTLL (R2 CTF9):
                                        SEQ ID NO: 10
GGCSEEDAL
```

```
-continued
(R1 CTF34):
                                        SEQ ID NO: 13
HFHGVSNLQEFRFMIGGGCSEEDAHVLVVAAAFV (R2 CTF34):
                                        SEQ ID NO: 14
HFYGVSNLQEFRYGLEGGCTDDTLHIFVVAGAFV
```

In certain embodiments of the diagnostic method, the dimeric form of the peptide is bound to carrier protein. In other embodiments, the dimeric form of the peptide is unbound.

In certain embodiments, the diagnostic method further comprises determining the level of adiponectin in a biological sample obtained from the subject and correlating the level of adiponectin with progression of the condition, onset of the condition, or efficacy of treatment of the condition.

In certain embodiments, the diagnostic method further comprises determining the level of bikunin in a biological sample obtained from the subject and correlating the level of bikunin with progression of the condition, onset of the condition, or efficacy of treatment of the condition.

In certain embodiments, the diagnostic method further comprises determining the level of the dimeric peptide in a biological sample obtained from the subject and correlating the level of dimeric peptide with progression of the condition, onset of the condition, or efficacy of treatment of the condition.

In certain embodiments, the diagnostic method further comprises determining the level of white blood cells in a biological sample obtained from the subject and correlating the level of white blood cells with progression of the condition, onset of the condition, or efficacy of treatment of the condition.

In certain embodiments, the diagnostic method further comprises determining the level of the dimeric peptide in a biological sample obtained from the subject and correlating the level of dimeric peptide with progression of the condition, onset of the condition, or efficacy of treatment of the condition.

In certain embodiments, the diagnostic method is for determining onset of the condition characterized by an adipocyte imbalance. In other embodiments, the diagnostic method is for determining progression of the condition characterized by an adipocyte imbalance. In yet other embodiments, the diagnostic method is for determining efficacy of treatment of the condition characterized by an adipocyte imbalance. In certain embodiments, the treatment is administration of a PPAR gamma agonist.

In certain embodiments of the diagnostic method, the condition is metabolic syndrome vascular blockage, diabetes type I, diabetes type II, arteriosclerosis, cardiovascular disease (including but not limited to, congestive heart failure, acute myocardial infarction, coronary artery disease, atherosclerosis, ischemia, or a combination thereof), insulin resistance, or a combination thereof.

The present invention provides methods for assaying for the presence or absence and/or determining the level of the peptides of the invention in bodily fluid. The phrase "determining the level" means detecting the presence or absence of an analyte in a sample or quantifying the amount in relative or absolute terms. A relative amount could be, for example, high, medium, or low. An absolute amount could reflect the measured strength of a signal or the translation of this signal strength into another quantitative format, such as micrograms/ml.

The monomeric, homodimeric, and heterodimeric forms of the C-terminal fragments of ADIPOR1 and ADIPOR2 useful in the methods, compositions, and kits of the invention can be detected by any suitable method. Detection paradigms that can be employed include, for example, optical methods, electrochemical methods (voltametry and amperometry techniques), atomic force microscopy, and radio frequency methods, e.g. multipolar resonance spectroscopy. Optical methods include, for example, colorimetric assays, electron impedance spectroscopy, and microscope, both confocal and non-confocal. detection of fluorescence, luminescence, chemiluminescence absorbance, reflectance, transmittance. and birefringence or refractive index, (e.g., surface plasmon resonance, ellipsometry, a resonant mirror method, a grating coupler waveguide method or interferometry).

In certain preferred embodiments, the level of expression, including presence or absence of monomeric, homodimeric, and heterodimeric forms of the C-terminal fragments of ADIPOR1 and ADIPOR2 of the invention, is assayed by an immunoassay. Those skilled in the art are aware that, in its broadest context, an "immunoassay" comprises incubating a test sample with one or more immunointeractive molecules specific for a target for a time and under conditions sufficient for binding thereto and detecting said binding. As used herein, the term "target" refers to the analyte that a probe is designed to bind. In certain preferred embodiments, the immunointeractive molecule will be an antibody. Conditions for incubating an antibody with a test sample vary, depending upon the format employed in the assay, the detection methods employed and the type and nature of the antibody molecule used m the assay. Those skilled in the art will recognize that any one of the commonly available immunological assay formats, for example radioimmunoassay, enzyme-linked immunosorbent assays (ELISA), immuno-tubimetric, and immunonephrometric. magnetic immuno particle separation, immunochromatography, immuno-microfluidic, immuno-centrifugal, diffusion-based Ouchterlony, rocket gel immunoelectrophoresis or in situ immunoassay can be readily adapted to the present purpose.

Immunoassays are useful in the quantification of the monomeric, homodimeric, and heterodimeric forms of the C-terminal fragments of ADIPOR1 and ADIPOR2 of the invention in a test sample, in particular to determine whether the level of the peptides of the invention is altered compared to normal levels detectable in non-diseased individuals. As a consequence, such an immunoassay is of particular use in determining whether a patient may have a disease or predisposition to disease. The immunoassay can have other uses as well, such as, for example, use in the monitoring of disease progression or monitoring of response to therapeutic interventions. The invention described herein extends to all such uses of immunointeractive molecules and diagnostic assays, which require said immunoassays for their performance.

By way of example only, in certain embodiments, an antibody raised against the fragment is immobilized onto a solid substrate to form a first complex and a biological test sample from a patient is brought into contact with the bound molecule. After a suitable period of incubation, for a period of time sufficient to allow formation of an antibody-secondary complex, a second antibody labeled with a reporter molecule capable of producing a detectable signal is then added and incubated, allow mg sufficient time for the formation of a tertiary complex. Any unreacted material is washed away, and the presence of the tertiary complex is determined by observation of a signal produced by the reporter molecule. The results can either be qualitative, by simple observation of the visible signal or may be quantitated by comparison with a control sample containing known amounts of hapten. Variations of this assay include a simultaneous assay, in winch both sample and labeled antibody are added simultaneously to the bound antibody, or a reverse assay in which the labeled antibody and sample to be tested are first combined, incubated, and then added simultaneously to the bound antibody. These techniques are well known to those skilled in the art and the possibility of variations will be readily apparent.

By "reporter molecule," as used in the present specification, is meant a molecule which, by its chemical nature, produces an analytically identifiable signal which allows the detection of antigen-bound antibody. Detection can be either qualitative or quantitative. The most commonly used reporter molecule in this type of assay are either colored latex particles, metal particles, enzymes, fluorophores or radionuclide containing molecules (i.e. radioisotopes).

The solid substrate is typically glass or a polymer, the most commonly used polymers being cellulose, polyacrylamide, nylon, nitrocellulose, polystyrene, polyvinyl chloride, or polypropylene. The solid supports may be in the form of strips, cassettes, tubes, beads, discs or microplates, or any other surface suitable for conducting an immunoassay. The binding processes are well-known in the art and generally consist of cross-linking, covalently binding, or physically adsorbing the molecule to the insoluble carrier.

A variety of immunoassay formats, including, for example, competitive and noncompetitive immunoassay formats, antigen capture assays and two-antibody sandwich assays can be used in the methods of the invention (Self and Cook, *Curr. Opin. Biotechnol.* 7:60-65 (1996)). In an antigen capture assay, antibody is bound to a solid phase, and sample is added such that a monomeric, homodimeric, or heterodimeric form of the C-terminal fragments of ADIPOR1 and ADIPOR2 of the invention is bound by the antibody. After unbound proteins are removed by washing, the amount of bound antigen can be quantitated, if desired, using, for example, a radioassay (Harfow and Lane, *Antibodies A Laboratory Manual*, Cold Spring Harbor Laboratory; New York. (1988)). Immunoassays can be performed under conditions of antibody excess, or as antigen competitions, to quantitate the amount of antigen and, thus, determine a level of the peptides of the invention.

Enzyme-linked immunosorbent assays (ELISAs) can be useful in certain methods of the invention. In the case of an enzyme immunoassay, an enzyme is conjugated to the second antibody, generally by means of glutaraldehyde or periodate. As will be readily recognized, however, a wide variety of different conjugation techniques exist which are readily available to one skilled in the art. Commonly used enzymes include, for example, horseradish peroxidase, glucose oxidase, β-galactosidase, and alkaline phosphatase, amongst others. The substrates to be used with the specific enzymes are generally chosen for the production, upon hydrolysis by the corresponding enzyme, of a detectable color change. It is also possible to employ fluorogenic substrates, for example, which yield a fluorescent product. An enzyme, such as horseradish peroxidase (HRP), alkaline phosphatase (AP), β-galactosidase, or urease, can be linked, for example, to an anti-adiponectin receptor C terminal fragment or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which can be used, for example, with the chromogenic substrate p-nitrophenyl phosphate to yield a soluble product readily detectable at 405 nm. Similarly, a β-galactosidase detection system can be used with, for example, the chromogenic substrate o-nitrophenyl-β-D-galactopyranoside (ONPG) to yield a soluble product detectable at 410 nm, or a urease detection system can be used with, for example, a substrate such as urea-bromocresol purple (Sigma Immunochemicals, St. Louis, Mo.). Useful enzyme-linked primary and secondary antibodies can be obtained from a number of commercial sources such as Jackson Immuno-Research (West Grove, Pa.).

In certain embodiments, the monomeric, homodimeric, and heterodimeric forms of the C-terminal fragments of ADIPOR1 and ADIPOR2 of the invention can be detected and measured using chemiluminescent detection. For example, in certain embodiments, antibodies specific for monomeric, homodimeric, and heterodimeric forms of the C-terminal fragments of ADIPOR1 and ADIPOR2 of the invention are used to capture the fragments present in the biological sample and a antibody specific for the specific antibodies and labeled with an chemiluminescent label is used to detect the fragments present in the sample. Any chemiluminescent label and detection system can be used in the present methods. Chemiluminescent secondary antibodies can be obtained commercially from various sources, such as Amersham. Methods of detecting chemiluminescent secondary antibodies are known in the art and are not discussed herein in detail.

Fluorescent detection also can be useful for detecting the peptides of the invention in certain methods of the invention. Useful fluorochromes include, for example, DAPI, fluorescein, lanthanide metals, Hoechst 33258, R-phycocyanin, B-phycoerythrin, R-phycoerythrin, rhodamine, Texas red, and lissamine. Fluorescein or rhodamine labeled α2-MG-, HA-, TIMP-1- or YKL-40 specific binding agents such as anti-α2-MG, anti-HA, anti-TIMP-1, or anti-YKL-40 antibodies, or fluorescein- or rhodamine-labeled secondary antibodies can be useful in the invention. Useful fluorescent antibodies can be obtained commercially, for example, from Tago Immunologicals {Burlingame, Calif.) as described further below. Fluorescent compounds can be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic color visually detectable with a light microscope.

Radioimmunoassays (RIAs) also can be useful in certain methods of the invention. Such assays are well known in the art. Radioimmunoassays can be performed, for example, with $^{125}$I-labeled primary or secondary antibody (Harlow and Lane, supra, 1988).

A signal from a detectable reagent can be analyzed, for example, using a spectrophotometer to detect color from a chromogenic substrate; a radiation counter to detect radiation, such as a gamma counter for detection of $^{125}$I, or a fluorometer to detect fluorescence in the presence of light of a certain wavelength. Where an enzyme-linked assay is used, quantitative analysis of the amount of the monomeric, homodimeric, and heterodimeric forms of the C-terminal fragments of ADIPOR1 and ADIPOR2 of the invention can be performed using a spectrophotometer such as an EMAX Microplate Reader {Molecular Devices; Menlo Park, Calif.) in accordance with the manufacturer's instructions. The assays of the invention can be automated or performed robotically, if desired, and that the signal from multiple samples can be detected simultaneously.

The methods of the invention also encompass the use of capillary electrophoresis based immunoassays (CEIA), which can be automated, if desired. Immunoassays also can be used in conjunction with laser-induced fluorescence as described, for example, in Schmalzing and Nashabeh, *Electrophoresis* 18:2184-93 (1997). and Bao, *J. Chromatogr. B, Biomed Sci.* 699:463-80 (1997). Liposome immunoassays, such as flow-injection liposome immunoassays and liposome immunosensors, also can be used to detect peptides of the invention or to determine a level of peptides of the invention according to certain methods of the invention (Rongen, et al., *J. Immunol. Methods* 204: 105-133 (1997)).

Sandwich enzyme immunoassays also can be useful in certain methods of the invention. In a two-antibody sandwich assay, a first antibody is bound to a solid support, and the antigen is allowed to bind to the first antibody. The amount of soluble C terminal adiponectin fragments can be quantitated by measuring the amount of a second antibody that hinds to it.

Quantitative western blotting also can be used to determine a level of soluble C terminal adiponectin fragments in a method of the invention. Western blots can be quantitated by well known methods such as scanning densitometry. As an example, protein samples are electrophoresed on 10% SDS-PAGE Laemmli gels. Primary murine monoclonal antibodies are reacted with the blot, and antibody binding confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear: Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., *J. Vasc. Surg.* 28:669-675 {1998}.

Levels of the peptides of the invention can also be determined using protein microarrays. Methods of producing protein microarrays that may be adapted for detecting levels of protein in a clinical sample are described in the art (see for example of Xiao, et al., (2005) *Mol. Cell. Endocrinol.;* 230 (1-2):95-10; Protein Microarrays (2004) Mark Schena (Ed) Jones & Bartlett Publishers, Inc.). U.S. Patent Publication 2003/0153013 describes methods of defecting proteins, e.g. antigens or antibodies, by immobilizing antibodies in a protein microarray on a membrane and contacting the microarray with detection proteins that can bind to the proteins to form protein complexes. Similarly, U.S. Patent Publication 2004/0038428 describes methods of constructing protein microarrays.

In certain preferred embodiments, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

Protein biochips are biochips adapted for the capture of peptides. Many protein biochips are described in the art. These include, for example, protein biochips produced by Ciphergen Biosystems, Inc. (Fremont, Calif.), Packard BioScience Company (Meriden, Conn.). Zyomyx (Hayward, Calif.), Phylos (Lexington, Mass.), and Biacore (Uppsala, Sweden). Examples of such protein biochips are described in the following patents or published patent applications: U.S. Pat. No. 6,225,047, WO 99/51773, U.S. Pat. No. 6,329,209, WO 00/56934 and U.S. Pat. No. 5,242,828, incorporated herein by reference in their entirety and for all purposes.

For use herein, the assay methods can involve capturing the peptides of the invention onto a solid substrate. Typically they will be captured using a biospecific capture reagent such as an antibody and, m particular, an antibody used in an immunoassay. Biospecific capture reagents include those molecules that bind a target analyte with an affinity of, for example, at least $10^{-9}$ M, $10^{-10}$ M, $10^{-11}$ M, or $10^{-12}$M. These molecules also can be captured with non-specific methods, such as chromatographic materials.

In certain embodiments of the present invention, the peptides of the invention will be detected by mass spectrometry. Examples of mass spectrometers are time-of-flight magnetic sector, quadrupole filter, ion trap, ion cyclotron resonance, electrostatic sector analyzer, and hybrids of these.

A preferred mass spectrometric technique for use in the invention is "Surface Enhanced Laser Desorption and Ionization" or "SELDI," as described, for example, in U.S. Pat. No. 5,719,060 and U.S. Pat. No. 6,225,047, each of which is incorporated herein by reference in its entirety and for all purposes. This refers to a method of desorption/ionization gas phase ion spectrometry (e.g. laser desorption/ionization mass spectrometry) in which an analyte is captured on the surface of a SELDI probe that engages the probe interface of the mass spectrometer.

One version of SELDI is called "affinity mass spectrometry." This version involves the use of probes comprising of an absorbent surface (an "affinity mass spectrometry probe"). In this context, "probe" refers to a device adapted to engage a probe interface and to present an analyte to ionizing energy for ionization and introduction into a mass spectrometer. A probe typically includes a solid substrate, either flexible or rigid, that has a sample-presenting surface, on which an analyte is presented to the source of ionizing energy.

Another version of SELDI is Surface-Enhanced Neat Desorption ("SEND"), which involves the use of probes comprising energy absorbing molecules attached to the probe surface ("SEND probe"). The phrase "Energy absorbing molecules" (EAM) denotes molecules that are capable of absorbing energy from a laser desorption/ionization source and, thereafter, contributing to desorption and ionization of analyte molecules in contact therewith. The EAM category includes molecules used in MALDI frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyacetophenone derivatives. In certain embodiments, the energy-absorbing molecule is incorporated into a linear or cross-linked polymer, e.g., a polymethacrylate. For example, the composition can be a co-polymer of a-cyano-4-methacryloyloxycinnamic acid and acrylate. In another embodiment, the composition is a co-polymer of a-cyano-4-methacrylyloylcinnamic acid, acrylate, and 3-(tri-ethoxy)silylpropyl methacrylate. In another embodiment, the composition is a co-polymer of a-cyano-4-methacryoyloxycinnamic acid and octadecyl-methacrylate ("C18 SEND"). SEND is further described in U.S. Pat. No. 6,124,137, incorporated herein by reference in its entirety and for all purposes.

A "selective surface" can be used to capture the fragments for SELDI analysis. The selective surface has an "adsorbent," also called a "binding moiety" or "capture reagent" attached to the surface. An "adsorbent" or "capture reagent" or "binding moiety," can be any material capable of binding an analyte. The capture reagent can be attached directly to the substrate of the selective surface, or the substrate can be a "reactive surface" that carries a "reactive moiety" that is capable of binding the capture reagent, e.g. through a reaction forming a covalent or coordinate covalent bond. Epoxide and carbodiimidazole are useful reactive moieties to covalently bind polypeptide capture reagents such as antibodies or cellular receptors. Nitriloacetic acid and iminodiacetic acid are useful reactive moieties that function as chelating agents to bind metal ions that interact non-covalently with histidine containing peptides.

In certain embodiments, the adsorbent used to capture the peptides of the invention comprises a biospecific capture reagent. A "biospecific adsorbent" refers to an adsorbent that binds to an analyte with an affinity of at least $10^{-9}$ M, $10^{-10}$ M, $10^{-11}$ M, or $10^{-12}$M. The preferred biospecific capture reagent is an antibody or a binding fragment thereof. This includes intact immunoglobulins and the variants arid portions of them well known in the art such as. Fab' fragments, F(ab')2 fragments, and scFv proteins. Other biospecific capture reagents include affibodies (Affibody, Teknikringen 30, floor 6, Box 700 04. Stockholm SE, 10044, Sweden, U.S. Pat. No. 5,831,012; see also Surface Logix, Inc., 50 Soldiers Held Place, Brighton, Mass. 02135 and Hodneland, C. D, et al., 2002, *Proc Natl. Acad. Sci.* 99: 5048-5052).

The fragments of the present invention can be captured on chromatographic adsorbents. "Chromatographic adsorbent" refers to an adsorbent material typically used in chromatography. Chromatographic adsorbents include, for example, nitrocellulose membranes, ion exchange materials, metal chelators (e.g., nitriloacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

In certain embodiments, a substrate with an adsorbent is contacted with the sample, e.g., patient serum, for a period of time sufficient to allow the target analytes that may be present to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties, an energy absorbing molecule then is applied to the substrate with the bound target analytes.

The biomolecules bound to the substrates can be detected in a gas phase ion spectrometer such as a time-of-flight mass spectrometer. The target analytes can be ionized by an ionization source such as a laser, the generated ions are collected by an ion optic assembly, and then a mass analyzer disperses and analyzes the passing ions. The detector then translates information of the detected ions into .mass-to-charge ratios. Detection of a target analyte typically will involve detection of signal intensity. Thus, both the quantity and mass of the target analyte can be determined.

In another mass spectrometry method, the target analytes can be first captured on a chromatographic resin having chromatographic properties that bind the target analytes, e.g., an antibody or antibodies, in the present example, this can include an immuno-chromatographic resin that comprises antibodies that bind C-terminal adiponectin receptor fragments. Unbound material can be washed from the resin. Then the target analytes can be eluted from the resin. Finally, the eluted target analytes can be detected by MALDI or by SELDI.

Analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses This reduces noise and increases dynamic range. This time-of-flight data is then subject to data processing.

Data generated by desorption and detection of target analytes can be analyzed with the use of a programmable digital computer. The computer program analyzes the data Io indicate the number of proteins detected, aid optionally the strength of the signal and the determined molecular mass for each target analyte detected. Data analysis can include steps of determining signal strength of a target analyte and removing data deviating from a predetermined statistical distribution. For example, the observed peaks can be normalized, by calculating the height of each peak relative to some reference. The reference can be background noise generated by the instrument and chemicals such as the energy absorbing molecule, which is set as zero in the scale.

Analysis generally involves the identification of peals in the spectrum that represent signal from an analyte. Peak selection can be done visually, but software is available that can automate the detection of peaks. In general, this software functions by identify signals having a signal-lo-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a large, analyte according to the present invention. The software also can subject the data regarding observed target analyte peaks to classification tree or ANN analysis, to determine whether a target analyte peak or combination of target analyte peaks is present that indicates cardiovascular disease status. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

This invention further provides antibodies that specifically bind to the C-terminal fragments of the adiponectin receptor. Methods of making antibodies having binding specificity to select peptides are well known in the art. For example, such antibodies can be selected by immunizing an animal with the target molecule, generating antibodies, and testing the antibodies to identify whether a particular antibody binds with the target molecule. Antibodies that bind with the target molecule can be selected. For example, one can generate monoclonal antibodies against these molecules.

The phrase "specifically binds to" refers to a binding reaction which is determinative of the presence of a target in the presence of a heterogeneous population of other biologics. Thus, under designated assay conditions, the specified binding region bind preferentially to a particular target and do not bind in a significant amount to other components present in a test sample. Specific binding to a target under such conditions can require a binding moiety that is selected for its specificity for a particular target. A variety of assay formats can be used to select binding regions that are specifically reactive with a particular analyte. Typically a specific or selective reaction will be at least twice background signal or noise and more typically more than 10 times background.

The term "antibody" is used in the broadest sense and specifically covers monoclonal antibodies, polyclonal antibodies, antibody compositions with polyepitopic specificity, bispecific antibodies, diabodies, chimeric, single-chain, and humanized antibodies, as well as antibody fragments (e.g., Fab, F(ab')$_2$, and Fv), so long as they exhibit the desired biological activity. Antibodies can be labeled for use in biological assays (e.g., radioisotope labels, fluorescent labels) to aid in detection of the antibody.

Antibodies can be labeled/conjugated to reporter molecules for use in biological assays (e.g., radioisotope labels, fluorescent labels) to aid in detection of the fragments described herein.

The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made by the hybridoma method first described by Kohler, et al., *Nature,* 256: 495, 1975, or can be made by recombinant DNA methods (see, e.g., U.S. Pat. No. 4,816,567, Cabilly, et al.). The "monoclonal antibodies" can also be isolated from phage antibody libraries using the techniques described in Clackson, et al., 624-628, 1991; Marks, et al., *J. Mol. Biol.,* 222: 581-597, 1991, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly, et al., supra; Morrison, et al., *Proc. Natl. Acad. Sci. U.S.A.,* 81: 6851-6855, 1984).

Monoclonal antibodies can be obtained by various techniques familiar to those skilled in the art. Briefly, spleen cells from an animal immunized with a desired antigen are immortalized, commonly by fusion with a myeloma cell (see, Kohler, et al., *Eur. J. Immunol.,* 6: 511-519, 1976). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells can be enhanced by various techniques, including injection into the peritoneal cavity of a vertebrate host. Alternatively, one can isolate DNA sequences which encode a monoclonal antibody or a binding fragment thereof by screening a DNA library from human B cells according to the general protocol outlined by Huse, et al., *Science,* 246: 1275-1281, 1989.

Monoclonal antibodies and polyclonal sera can be collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better.

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones, et al., *Nature,* 321: 522-525, 1986; Reichmann, et al., *Nature,* 332: 323-329, 1988; Presta, *Curr. Op. Struct. Biol.,* 2: 593-596, 1992. The humanized antibody includes a Primatized™ antibody wherein the antigen-binding region of the antibody is derived from an antibody produced by immunizing macaque monkeys with the antigen of interest.

A number of immunogens comprising portions of the fragments described herein can be used to produce antibodies specifically reactive with the fragments. For example, a fragment of the present invention, can be isolated using techniques known in the art. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein can also be used either in pure or impure form. The product is then injected into an animal capable of producing antibodies. Either monoclonal or polyclonal antibodies can be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

In a further embodiment, antibodies or antibody fragments can be isolated from antibody phage libraries generated using the techniques described in McCafferty, et al., *Nature,* 348: 552-554, 1990; Clackson, et al., *Nature,* 352: 624-628, 1991; Marks, et al., *J. Mol. Biol.,* 222: 581-597, 1991, describe the isolation of murine and human antibodies, respectively, using phage libraries. Subsequent publications describe the production of high affinity (nM range) human antibodies by chain shuffling (Mark, et al., *Bio/Technology,* 10: 779-783, 1992), as well as combinatorial infection and in vivo recombination as a strategy for constructing very large phage libraries (Waterhouse, et al., *Nuc. Acids. Res.,* 21: 2265-2266, 1993). Thus, these techniques are viable alternatives to traditional monoclonal antibody hybridoma techniques for isolation of monoclonal antibodies.

In certain embodiments, the antibodies are selected to distinguish between one fragment of C-terminal adiponectin receptor and another, that is, the antibodies are selected that specifically bind to one form, but not another, under the same assay conditions.

Accordingly, the present invention provides an antibody that specifically binds to an epitope of an adiponectin receptor fragment having SEQ ID NO:1, SEQ ID NO:2, SEQ ID NO:5, or SEQ ID NO:6.

In certain embodiments, the condition is metabolic syndrome, diabetes (including type I diabetes, type II diabetes, and gestational diabetes), cardiovascular disease (including congestive heart failure, acute myocardial infarction, coronary artery disease, vascular blockage, arteriosclerosis, atherosclerosis, ischemia, or combinations thereof), insulin resistance, and Alzheimer's disease.

Accordingly, the present invention is directed, in part, to methods of treating diabetes in a patient in need thereof, comprising the step of:
  administering to said patient an effective amount of a peptide or a pharmaceutically-acceptable salt thereof;
  wherein said peptide is selected from the group consisting of:
    a monomeric peptide having at least about 75% identity with SEQ ID NO:2;
    a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
    a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
    a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;

a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;

a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;

a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;

a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;

a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;

a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In other embodiments, the invention is directed to methods of treating abnormal adipocyte activity in a patient in need thereof, comprising the step of:

administering to said patient an effective amount of a peptide or a pharmaceutically-acceptable salt thereof;

wherein said peptide is selected from the group consisting of:

a monomeric peptide having at least about 75% identity with SEQ ID NO:2;

a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;

a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;

a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;

a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;

a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;

a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;

a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;

a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;

a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In another embodiment, the invention is directed to methods of treating insulin resistance in a patient in need thereof, comprising the step of:
  administering to said patient an effective amount of a peptide or a pharmaceutically-acceptable salt thereof;
wherein said peptide is selected from the group consisting of:
  a monomeric peptide having at least about 75% identity with SEQ ID NO:2;
  a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
  a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
  a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
  a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
  a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
  a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
  a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;
  a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;
  a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;
  a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;
  a dimer of said first heterodimer;
  a dimer of said first homodimer;
  a dimer of said second homodimer;
  a dimer of said second heterodimer;
  a dimer of said third homodimer;
  a dimer of said fourth homodimer;
  a dimer of said third heterodimer;
  a dimer of said fourth heterodimer;
  a dimer of said fifth heterodimer; and
  a dimer of said sixth heterodimer.

In yet other embodiments, the invention is directed to methods of treating metabolic syndrome in a patient in need thereof; comprising the step of:
  administering to said patient an effective amount of a peptide or a pharmaceutically-acceptable salt thereof;
wherein said peptide is selected from the group consisting of:
  a monomeric peptide having at least about 75% identity with SEQ ID NO:2;
  a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
  a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
  a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
  a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
  a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
  a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
  a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;
  a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;

a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In certain embodiments of the invention, the patient suffers from type I or type II diabetes. In other embodiments of the invention, patient suffers from gestational diabetes.

In yet other embodiments, the invention is directed to methods of inhibiting insulin degradation enzyme (IDE) in a patient, comprising the step of:

administering to said patient an effective amount of a peptide or a pharmaceutically-acceptable salt thereof;

wherein said peptide is selected from the group consisting of:

a monomeric peptide having at least about 75% identity with SEQ ID NO:2;

a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;

a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;

a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;

a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;

a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;

a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;

a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;

a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;

a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In other embodiments, the invention is directed to methods of treating Alzheimer's disease in a patient, comprising the step of:

administering to said patient an effective amount of a peptide or a pharmaceutically-acceptable salt thereof;

wherein said peptide is selected from the group consisting of:

a monomeric peptide having at least about 75% identity with SEQ ID NO:2;

a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;

a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;

a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;

a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;

a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;

a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;

a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;

a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;

a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In other embodiments, the invention is directed to methods of treating cardiovascular disease associated with adiponectin levels in a patient, comprising the step of:
administering to said patient an effective amount of a peptide or a pharmaceutically-acceptable salt thereof;
wherein said peptide is selected from the group consisting of:

a monomeric peptide having at least about 75% identity with SEQ ID NO:2;

a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;

a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;

a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;

a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;

a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;

a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;

a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;

a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;

a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In yet other embodiments, the invention is directed to methods of inhibiting ADAM-17 enzyme in a patient, comprising the step of:

administering to said patient an effective amount of a peptide or a pharmaceutically-acceptable salt thereof;

wherein said peptide is selected from the group consisting of:
- a monomeric peptide having at least about 75% identity with SEQ ID NO:2;
- a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
- a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
- a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
- a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
- a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
- a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
- a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;
- a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;
- a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;
- a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;
- a dimer of said first heterodimer;
- a dimer of said first homodimer;
- a dimer of said second homodimer;
- a dimer of said second heterodimer;
- a dimer of said third homodimer;
- a dimer of said fourth homodimer;
- a dimer of said third heterodimer;
- a dimer of said fourth heterodimer;
- a dimer of said fifth heterodimer; and
- a dimer of said sixth heterodimer.

Thus, peptides of the invention are useful as an anti-TNF alpha therapy and as an anti-HER2 neu therapy. Anti-TNF alpha therapy is important in treating inflammation and autoimmune diseases, such as lupus, rheumatoid arthritis, and type-1 diabetes. Anti-HER2 neu therapy is important in impacting tumor growth, especially in breast cancer.

In yet other embodiments, the invention is directed to methods of treating a condition associated with TNF-alpha in a patient, comprising the step of:

administering to said patient an effective amount of a peptide or a pharmaceutically-acceptable salt thereof;

wherein said peptide is selected from the group consisting of:
- a monomeric peptide having at least about 75% identity with SEQ ID NO:2;
- a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
- a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
- a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
- a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
- a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
- a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
- a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;

a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;

a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In yet other embodiments, the invention is directed to methods of treating a condition associated with HER2 neu in a patient, comprising the step of:

administering to said patient an effective amount of a peptide or a pharmaceutically-acceptable salt thereof;

wherein said peptide is selected from the group consisting of:

a monomeric peptide having at least about 75% identity with SEQ ID NO:2;

a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;

a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;

a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;

a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;

a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;

a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;

a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;

a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;

a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In yet other embodiments, the invention is directed to methods of inhibiting a protease in a patient, comprising:

administering to said patient an effective amount of a peptide or a pharmaceutically-acceptable salt thereof;

wherein said peptide is selected from the group consisting of:

a monomeric peptide having at least about 75% identity with SEQ ID NO:1;

a monomeric peptide having at least about 75% identity with SEQ ID NO:2;

a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;

a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;

a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;
a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;
a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;
a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;
a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer; and
wherein said protease is insulysin/insulin degradation enzyme (IDE), ADAM-17 peptidase, omptin, aureolysin, falcilysin, pepsin A, pepsin B, cathespsin D, cathepsin E, cathespsin G, cathepsin H, cathepsin L, acrocylindropepsin, acid peptidase (*Cladosporium*), rhodotorulapepsin, grifolisin, physarolisin, peptidase K, subtilisin aprM, subtilisin BPN', high alkaline protease, M-peptidase sp. KSM-K16, subtilisin Carlsberg, meprinpeptidase, streptogrisin B, chymotrypsin C, peptidase Ci, camelysis, deuterolysin, aminopeptidase Ap1, endothelin-converting enzyme 1, neprilysin, leucolysisn, presenilin, thermopsin, retropepsin (human Tcell leukemia virus), bovine immunodeficiency virus retropepsin, candidapepsin SAP2, candidapepsin SAP3, candidapepsin SAP6, candiparapsin SAP1, or rhizopuspepsin, provided that said protease is not IDE or ADAM-17 peptidase when said peptide is a monomeric peptide having at least about 75% identity with SEQ ID NO:1.

In yet other embodiments, the invention is directed to methods of treating insulin resistance in a patient in need thereof, comprising the step of:
administering to said patient an effective amount of a peptide or a pharmaceutically-acceptable salt thereof;
wherein said peptide is selected from the group consisting of:
a monomeric peptide having at least about 75% identity with SEQ ID NO:2;
a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;
a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;
a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;
a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In yet other embodiments, the invention is directed to methods of causing insulin secretion in a patient, comprising the step of:
administering to said patient an effective amount of a peptide or a pharmaceutically-acceptable salt thereof;
wherein said peptide is selected from the group consisting of:
a monomeric peptide having at least about 75% identity with SEQ ID NO:2;
a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;
a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;
a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;
a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;
a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;
a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;
a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;
a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In certain embodiments, the patient suffers from diabetes. In other embodiments, the patient suffers from abnormal adipocyte activity. In yet other embodiments, the patient suffers from insulin resistance. In certain embodiments, the patient suffers from metabolic syndrome.

In yet other embodiments, the invention is directed to methods of increasing insulin level in a patient, wherein said patient does not suffer from diabetes, comprising the step of:
administering to said patient an effective amount of a peptide or a pharmaceutically-acceptable salt thereof;
wherein said peptide is selected from the group consisting of:
a monomeric peptide having at least about 75% identity with SEQ ID NO:2;
a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;
a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;
a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;
a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;

a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;

a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;

a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;

a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;

a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer.

In certain instances, the monomeric, homodimeric, and heterodimeric forms of the C-terminal fragments of ADIPOR1 and ADIPOR2 useful in the methods, compositions, dosage forms, and kits of the invention do not have the exact sequence as described herein, but are present as a variant form. For example, the monomeric, homodimeric, and heterodimeric forms of the C-terminal fragments of ADIPOR1 and ADIPOR2 of the invention can substitute at least about 5%, at least about 10%, or even at least about 25% of their amino acids without having a loss of function. Accordingly, at least some of the amino acids in the peptides of the heterodimers can be substituted with other amino acids.

In certain embodiments of the invention, the monomeric peptide has at least about 78% identity with SEQ ID NO:1, preferably, the monomeric peptide has at least about 81% identity with SEQ ID NO:1, more preferably, the monomeric peptide has at least about 84% identity with SEQ ID NO:1, yet even more preferably, the monomeric peptide has at least about 87% identity with SEQ ID NO:1, even more preferably, the monomeric peptide has at least about 90% identity with SEQ ID NO:1, yet even more preferably, the monomeric peptide has at least about 93% identity with SEQ ID NO:1, and still more preferably, the monomeric peptide has at least about 96% identity with SEQ ID NO:1.

In certain embodiments of the invention where the peptide is heterodimer of a CTF32, the first mer unit has at least about 78% identity with SEQ ID NO:1 and the second mer unit has at least about 78% identity with SEQ ID NO:2, preferably, the first mer unit has at least about 81% identity with SEQ ID NO:1 and the second mer unit has at least about 81% identity with SEQ ID NO:2, more preferably, the first mer unit has at least about 84% identity with SEQ ID NO:1 and the second mer unit has at least about 84% identity with SEQ ID NO:2, yet even more preferably, the first mer unit has at least about 87% identity with SEQ ID NO:1 and the second mer unit has at least about 87% identity with SEQ ID NO:2, even more preferably, the first mer unit has at least about 90% identity with SEQ ID NO:1 and the second mer unit has at least about 90% identity with SEQ ID NO:2, yet even more preferably, the first mer unit has at least about 93% identity with SEQ ID NO:1 and the second mer unit has at least about 93% identity with SEQ ID NO:2, and still more preferably, the first mer unit has at least about 96% identity with SEQ ID NO:1 and the second mer unit has at least about 96% identity with SEQ ID NO:2.

In certain embodiments of the invention where the peptide is homodimer of R1 CTF32, the first mer unit has at least about 78% identity with SEQ ID NO:1 and the second mer unit has at least about 78% identity with SEQ ID NO:1, preferably, the first mer unit has at least about 81% identity with SEQ ID NO:1 and the second mer unit has at least about 81% identity with SEQ ID NO:1, more preferably, the first mer unit has at least about 84% identity with SEQ ID NO:1 and the second mer unit has at least about 84% identity with SEQ ID NO:1, yet even more preferably, the first mer unit has at least about 87% identity with SEQ ID NO:1 and the second mer unit has at least about 87% identity with SEQ ID NO:1, even more preferably, the first mer unit has at least about 90% identity with SEQ ID NO:1 and the second mer unit has at least about 90% identity with SEQ ID NO:1, yet even more preferably, the first mer unit has at least about 93% identity with SEQ ID NO:1 and the second mer unit has at least about 93% identity with SEQ ID NO:1, and still more preferably, the first mer unit has at least about 96% identity with SEQ ID NO:1 and the second mer unit has at least about 96% identity with SEQ ID NO:1.

In certain embodiments of the invention where the peptide is homodimer of R2 CTF32, the first mer unit has at least about 78% identity with SEQ ID NO:2 and the second mer unit has at least about 78% identity with SEQ ID NO:2, preferably, the first mer unit has at least about 81% identity with SEQ ID NO:2 and the second mer unit has at least about 81% identity with SEQ ID NO:2, more preferably, the first mer unit has at least about 84% identity with SEQ ID NO:2 and the second mer unit has at least about 84% identity with SEQ ID NO:2, yet even more preferably, the first mer unit has at least about 87% identity with SEQ ID NO:2 and the second mer unit has at least about 87% identity with SEQ ID NO:2, even more preferably, the first mer unit has at least about 90% identity with SEQ ID NO:2 and the second mer unit has at least about 90% identity with SEQ ID NO:2, yet even more preferably, the first mer unit has at least about 93% identity with SEQ ID NO:2 and the second mer unit has at least about 93% identity with SEQ ID NO:2, and still more preferably, the first mer unit has at least about 96% identity with SEQ ID NO:2 and the second mer unit has at least about 96% identity with SEQ ID NO:2.

In certain embodiments of the invention where the peptide is heterodimer of a R1 CTF25 and a R2 CTF25, the first mer unit has at least about 80% identity with SEQ ID NO:5 and the second mer unit has at least about 80% identity with SEQ ID NO:6, preferably, the first mer unit has at least about 85% identity with SEQ ID NO:5 and the second mer unit has at least about 85% identity with SEQ ID NO:6, more preferably, the first mer unit has at least about 90% identity with SEQ ID NO:5 and the second mer unit has at least about 90% identity with SEQ ID NO:6, yet even more preferably, the first mer unit has at least about 95% identity with SEQ ID NO:5 and the second mer unit has at least about 95% identity with SEQ ID NO:6, even more preferably, the first mer unit has at least about 98% identity with SEQ ID NO:5 and the second mer unit has at least about 98% identity with SEQ ID NO:6.

In certain embodiments of the invention where the peptide is homodimer of R1 CTF 25, the first mer unit has at least about 80% identity with SEQ ID NO:5 and the second mer unit has at least about 80% identity with SEQ ID NO:5, preferably, the first mer unit has at least about 85% identity with SEQ ID NO:5 and the second mer unit has at least about 85% identity with SEQ ID NO:5, more preferably, the first mer unit has at least about 90% identity with SEQ ID NO:5 and the second mer unit has at least about 90% identity with SEQ ID NO:5, yet even more preferably, the first mer unit has at least about 95% identity with SEQ ID NO:5 and the second mer unit has at least about 95% identity with SEQ ID NO:5, even more preferably, the first mer unit has at least about 98% identity with SEQ ID NO:5 and the second mer unit has at least about 98% identity with SEQ ID NO:5.

In certain embodiments of the invention where the peptide is homodimer of R2 CTF 25, the first mer unit has at least about 80% identity with SEQ ID NO:6 and the second mer unit has at least about 80% identity with SEQ ID NO:6, preferably, the first mer unit has at least about 85% identity with SEQ ID NO:6 and the second mer unit has at least about 85% identity with SEQ ID NO:6, more preferably, the first mer unit has at least about 90% identity with SEQ ID NO:6 and the second mer unit has at least about 90% identity with SEQ ID NO:6, yet even more preferably, the first mer unit has at least about 95% identity with SEQ ID NO:6 and the second mer unit has at least about 95% identity with SEQ ID NO:6, even more preferably, the first mer unit has at least about 98% identity with SEQ ID NO:6 and the second mer unit has at least about 98% identity with SEQ ID NO:6.

In certain embodiments of the invention where the peptide is a heterodimer of a R1 CTF25 and a R1 CTF32, the first mer unit has at least about 80% identity with SEQ ID NO:1 and the second mer unit has at least about 80% identity with SEQ ID NO:5, preferably, the first mer unit has at least about 85% identity with SEQ ID NO:1 and the second mer unit has at least about 85% identity with SEQ ID NO:5, more preferably, the first mer unit has at least about 90% identity with SEQ ID NO:1 and the second mer unit has at least about 90% identity with SEQ ID NO:5, yet even more preferably, the first mer unit has at least about 95% identity with SEQ ID NO:1 and the second mer unit has at least about 95% identity with SEQ ID NO:5, even more preferably, the first mer unit has at least about 98% identity with SEQ ID NO:1 and the second mer unit has at least about 98% identity with SEQ ID NO:5.

In certain embodiments of the invention where the peptide is a heterodimer of a R2 CTF25 and a R1 CTF32, the first mer unit has at least about 80% identity with SEQ ID NO:1 and the second mer unit has at least about 80% identity with SEQ ID NO:6, preferably, the first mer unit has at least about 85% identity with SEQ ID NO:1 and the second mer unit has at least about 85% identity with SEQ ID NO:6, more preferably, the first mer unit has at least about 90% identity with SEQ ID NO:1 and the second mer unit has at least about 90% identity with SEQ ID NO:6, yet even more preferably, the first mer unit has at least about 95% identity with SEQ ID NO:1 and the second mer unit has at least about 95% identity with SEQ ID NO:6, even more preferably, the first mer unit has at least about 98% identity with SEQ ID NO:1 and the second mer unit has at least about 98% identity with SEQ ID NO:6.

In certain embodiments of the invention where the peptide is a heterodimer of a R1 CTF25 and a R2 CTF32, the first mer unit has at least about 80% identity with SEQ ID NO:2 and the second mer unit has at least about 80% identity with SEQ ID NO:5, preferably, the first mer unit has at least about 85% identity with SEQ ID NO:2 and the second mer unit has at least about 85% identity with SEQ ID NO:5, more preferably, the first mer unit has at least about 90% identity with SEQ ID NO:2 and the second mer unit has at least about 90% identity with SEQ ID NO:5, yet even more preferably, the first mer unit has at least about 95% identity with SEQ ID NO:2 and the second mer unit has at least about 95% identity with SEQ ID NO:5, even more preferably, the first mer unit has at least about 98% identity with SEQ ID NO:2 and the second mer unit has at least about 98% identity with SEQ ID NO:5.

In certain embodiments of the invention where the peptide is heterodimer of a R2 CTF25 and a R2 CTF32, the first mer unit has at least about 80% identity with SEQ ID NO:2 and the second mer unit has at least about 80% identity with SEQ ID NO:6, preferably, the first mer unit has at least about 85% identity with SEQ ID NO:2 and the second mer unit has at least about 85% identity with SEQ ID NO:6, more preferably, the first mer unit has at least about 90% identity with SEQ ID NO:2 and the second mer unit has at least about 90% identity with SEQ ID NO:6, yet even more preferably, the first mer unit has at least about 95% identity with SEQ ID NO:2 and the second mer unit has at least about 95% identity with SEQ ID NO:6, even more preferably, the first mer unit has at least about 98% identity with SEQ ID NO:2 and the second mer unit has at least about 98% identity with SEQ ID NO:6.

In certain embodiments, the methods are directed to treating patients suffering from diabetes. In certain embodiments, the methods are directed to treating patients suffering from abnormal adipocyte activity. In certain embodiments, the methods are directed to treating patients suffering from insulin resistance. In certain embodiments, the methods are directed to treating patients suffering from metabolic syndrome.

In certain embodiments of the invention, the peptide or pharmaceutically-acceptable salt thereof is administered via a parenteral route. In certain preferred embodiments, the peptide or pharmaceutically-acceptable salt thereof is administered via injection. In other preferred embodiments, the peptide or pharmaceutically-acceptable salt thereof is administered via infusion. In yet other preferred embodiments, the peptide or pharmaceutically-acceptable salt thereof is administered via inhalation.

In another embodiment, the invention is directed to compositions, comprising:
  a peptide or a pharmaceutically-acceptable salt thereof;
wherein said peptide is selected from the group consisting of:
    a monomeric peptide having at least about 75% identity with SEQ ID NO:2;
    a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;

a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;

a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;

a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;

a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;

a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;

a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;

a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;

a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer; and
at least one pharmaceutically-acceptable carrier.

In further embodiments, the invention is directed to compositions, comprising:

a purified peptide or a pharmaceutically-acceptable salt thereof;

wherein said peptide is selected from the group consisting of:

a monomeric peptide having at least about 75% identity with SEQ ID NO:2;

a first heterodimer comprising a first mer unit and a second mer unit, wherein said first mer unit has at least about 75% identity with SEQ ID NO:1 and wherein said second mer unit has at least about 75% identity with SEQ ID NO:2, and wherein said first mer unit and said second mer unit are linked via a disulfide bond;

a first homodimer comprising a first mer unit and a second mer unit, wherein said first mer unit has at least about 75% identity with SEQ ID NO:1 and wherein said second mer unit has at least about 75% identity with SEQ ID NO:1, and wherein said first mer unit and said second mer unit are linked via a disulfide bond;

a second homodimer comprising a first mer unit and a second mer unit, wherein said first mer unit has at least about 75% identity with SEQ ID NO:2 and wherein said second mer unit has at least about 75% identity with SEQ ID NO:2, and wherein said first mer unit and said second mer unit are linked via a disulfide bond;

a second heterodimer comprising a first mer unit and a second mer unit, wherein said first mer unit has at least about 75% identity with SEQ ID NO:5 and wherein said second mer unit has at least about 75% identity with SEQ ID NO:6, and wherein said first mer unit and said second mer unit are linked via a disulfide bond;

a third homodimer comprising a first mer unit and a second mer unit, wherein said first mer unit has at least about 75% identity with SEQ ID NO:5 and wherein said second mer unit has at least about 75% identity with SEQ ID NO:5, and wherein said first mer unit and said second mer unit are linked via a disulfide bond;

a fourth homodimer comprising a first mer unit and a second mer unit, wherein said first mer unit has at least about 75% identity with SEQ ID NO:6 and wherein said second mer unit has at least about 75% identity with SEQ ID NO:6, and wherein said first mer unit and said second mer unit are linked via a disulfide bond;

a third heterodimer comprising a first mer unit and a second mer unit, wherein said first mer unit has at least about 75% identity with SEQ ID NO:1 and wherein said second mer unit has at least about 75% identity with SEQ ID NO:5, and wherein said first mer unit and said second mer unit are linked via a disulfide bond;

a fourth heterodimer comprising a first mer unit and a second mer unit, wherein said first mer unit has at least about 75% identity with SEQ ID NO:1 and wherein said second mer unit has at least about 75% identity with SEQ ID NO:6, and wherein said first mer unit and said second mer unit are linked via a disulfide bond;

a fifth heterodimer comprising a first mer unit and a second mer unit, wherein said first mer unit has at least about 75% identity with SEQ ID NO:2 and wherein said second mer unit has at least about 75% identity with SEQ ID NO:5, and wherein said first mer unit and said second mer unit are linked via a disulfide bond;

a sixth heterodimer comprising a first mer unit and a second mer unit, wherein said first mer unit has at least about 75% identity with SEQ ID NO:2 and wherein said second mer unit has at least about 75% identity with SEQ ID NO:6, and wherein said first mer unit and said second mer unit are linked via a disulfide bond;
a dimer of said first heterodimer;
a dimer of said first homodimer;
a dimer of said second homodimer;
a dimer of said second heterodimer;
a dimer of said third homodimer;
a dimer of said fourth homodimer;
a dimer of said third heterodimer;
a dimer of said fourth heterodimer;
a dimer of said fifth heterodimer; and
a dimer of said sixth heterodimer;
optionally, at least one pharmaceutically-acceptable carrier.

In yet other embodiments, the invention is directed to injectable dosage forms, comprising:
the composition described herein; and
at least one solvent for said peptide.

In other embodiments, the invention is directed to inhalable dosage forms, comprising:
the composition described herein; and
at least one pharmaceutically-acceptable carrier for administration of said peptide via inhalation.

In another embodiment, the invention is directed to kits, comprising:
instructions for administering an injectable dosage form to a patient;
a container comprising a composition described herein;
a container comprising a pharmaceutically-acceptable solvent for said compositions.

In other embodiments, the invention is directed to kits, comprising:
instructions for administering an inhalable dosage form to a patient;
a container comprising a composition described herein;
a container comprising a pharmaceutically-acceptable solvent for said composition.

In certain embodiments of the invention, the composition is lyophilized.

A pharmaceutical composition of the invention is formulated to be compatible with its intended route of administration, which is preferably a parenteral route, especially intravenous (via injection or via infusion) or via inhalation. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents, such as benzyl alcohol or methyl parabens; antioxidants, such as ascorbic acid or sodium bisulfite; chelating agents, such as ethylenediaminetetraacetic acid; buffers, such as acetates, citrates, or phosphates, and agents for adjusting tonicity, such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate-buffered saline (PBS). In all cases, the composition must be sterile and should be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, a pharmaceutically-acceptable polyol like glycerol, propylene glycol, liquid polyethylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols, such as mannitol, sorbitol, and sodium chloride in the composition. Prolonged absorption of the injectable composition can be brought about by including in the composition an agent that delays absorption, for example, aluminum monostearate and gelatin. Sterile injectable solutions can be prepared by incorporating the active ingredient (i.e., the polypeptide) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the other required ingredients from those enumerated above. In the case of sterile powders for the preparation of sterile injectable solutions, the preferred methods of preparation are vacuum drying and freeze-drying, which yield a powder of the active ingredient plus and desired ingredients from a previously sterile-filtered solution thereof.

For administration via inhalation, the peptides are delivered in the form of an aerosol spray from a pressurized container or dispenser that contains a suitable propellant, e.g., a gas such as carbon dioxide, or a nebulizer.

It is especially advantageous to formulate the compositions in dosage unit form for ease of administration and uniformity of dosage. Dosage unit form, as used herein, refers to physically discrete units suited as unitary dosages for the patient to be treated; each unit containing a predetermined quantity of the peptide calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of the patients.

The pharmaceutical compositions can be included in a container, pack, or dispenser together with instructions for administration.

In certain embodiments of the invention, the compositions further comprise at least one pharmaceutically-acceptable carrier. In certain preferred embodiments, the pharmaceutically-acceptable carrier is sodium lactate. Other pharmaceutical carriers useful in the solutions and compositions useful in the practice of the present invention include, but are not limited to, proteins, peptides, amino acids, lipids, polymers, and carbohydrates (e.g., sugars, including monosaccharides, di-, tri-, terra-, and oligosaccharides; derivatized sugars such as alditols, aldonic acids, esterified sugars; and polysaccharides or sugar polymers), which may be present singly or in combination. Exemplary protein carriers include serum albumin such as human serum albumin (HSA), recombinant human albumin (rHA), gelatin, and casein. Representative amino acid/polypeptide components, which may also function in a buffering capacity, include alanine, glycine, arginine, betaine, histidine, glutamic acid, aspartic acid, cysteine, lysine, leucine, proline, isoleucine, valine, methionine, phenylalanine, and aspartame. Polyamino acids of the representative amino acids such as di-leucine and tri-leucine are also suitable for use with the present invention. Carbohydrate carriers suitable for use in the invention include, for example, monosaccharides such as fructose, maltose, galactose, glucose, D-mannose, and sorbose; disaccharides, such as lactose, sucrose, trehalose, cellobiose; polysaccharides, such as raffinose, melezitose, maltodextrins, dextrans, and starches; and alditols, such as mannitol, xylitol, maltitol, lactitol, xylitol sorbitol (glucitol), and myoinositol. Additionally, the solutions and compositions useful in the invention may include polymeric carriers such as polyvinylpyrrolidones, hydroxypropyl methylcellulose, methylcellulose, ethylcellulose, Ficolls (a polymeric sugar), dextran, dextrates (e.g., cyclodextrins, such as 2-hydroxypropyl-P-cyclodextrin, hydroxyethyl starch), polyethylene glycols, pectin, salts (e.g., sodium chloride), antioxidants, antistatic agents, surfactants (e.g., polysorbates such as "TWEEN 20" and "TWEEN 80", lecithin, oleic acid, benzalkonium chloride, and sorbitan esters), lipids (e.g., phospholipids, fatty acids), steroids (e.g., cholesterol), and chelating agents (e.g., EDTA). Other examples of pharmaceutical carriers and/or additives suitable for use in the solutions and compositions of the invention are listed in *Remington: The Science & Practice of Pharmacy*, 20th ed., Williams & Williams, (2000), and in the *Physician's Desk Reference*, 52nd ed., Medical Economics, Montvale, N.J. (1998), the disclosures of which are herein incorporated by reference.

In certain embodiments of the invention, the pharmaceutically-acceptable solvent for the peptides of the invention or a pharmaceutically-acceptable salt thereof is water, aqueous sodium chloride solution, aqueous potassium chloride solution, aqueous magnesium chloride hexahydrate solution, aqueous sodium acetate trihydrate solution, aqueous sodium gluconate solution, aqueous sodium hydroxide solution, aqueous dextrose solution, Lactated Ringer's solution, or a combination thereof. In certain embodiments of the invention, the pharmaceutically-acceptable solvent for the peptides of the invention or a pharmaceutically-acceptable salt thereof is aqueous alcohol, such as, for example, 20% ethanol.

In certain embodiments of the invention, the solution comprising the peptides of the invention or a pharmaceutically-acceptable salt thereof has a pH of about 3.5 to about 5.5. The solution may also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers.

In certain embodiments of the invention, the peptides of the invention and pharmaceutically-acceptable salts thereof or compositions comprising these heterodimers are lyophilized.

The various dosage forms are prepared in accordance with acceptable pharmaceutical procedures, such as described in *Remington: The Science and Practice of Pharmacy*, 20th ed.; Gennaro, A. R., Ed.; Lippincott Williams & Wilkins: Philadelphia, Pa., (2000).

In addition, the compositions of the invention may further comprise a second active ingredient in addition to the peptides of the invention or its pharmaceutically acceptable salt, which is useful for the concurrent or synergistic treatment of diabetes, abnormal adipocyte activity, and insulin resistance. These compounds, and compositions thereof, may include additional compounds known to be useful for the treatment of diabetes, abnormal adipocyte activity, and insulin resistance. Suitable additional compounds include sulfonylureas, meglitinides, biguanides, thiazolidinediones, DPP-4 Inhibitors, alpha-glucosidase inhibitors, glucagons like-peptide (GLP-1)/exendin-4, and combinations thereof.

The peptides of the invention or its pharmaceutically acceptable salt of the invention may be prepared in a number of ways well known to those skilled in the art. The peptides of the invention and their pharmaceutically acceptable salts can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

The heterodimers useful in the invention may be prepared recombinantly or synthesized by conventional methods in liquid-phase or solid-phase, using manual or automated techniques. Suitable methods are described generally, for example, in:

Atherton, E. and Sheppard, R. C., *Solid Phase peptide synthesis: a practical approach*. Oxford, England: IRL Press (1989);

Stewart, J. M. and Young, J. D., *Solid phase peptide synthesis, 2nd edition*, Rockford: Pierce Chemical Company, 91 (1984);

R. B. Merrifield, "Solid Phase Peptide Synthesis. I. The Synthesis of a Tetrapeptide," *J. Am. Chem. Soc.* 85 (14): 2149-2154 (1963); and L. A. Carpino "1-Hydroxy-7-azabenzotriazole. An efficient peptide coupling additive," *J. Am. Chem. Soc.* 115 (10): 4397-4398 (1993);

which are incorporated herein by reference. Additionally, any portion of the amino acid sequence of the peptides can be altered during direct synthesis and/or combined using chemical methods with sequences with other proteins to produce a variant peptide.

Preferably, the peptides are prepared by conventional solid-phase peptide synthesis methodology. Standard synthesis protocols based on Fmoc chemistry may be used. After synthesis, the crude peptides are cleaved from the solid support and side-chain protecting groups are removed. The crude peptides can be purified, for example, by preparative high performance liquid chromatography, such as C18 reverse-phase HPLC. The purified peptide can be further desalted by HPLC and lyophilized to dry form. Preferable, the peptides are stored in sealed containers under nitrogen.

All forms of the peptides of the invention, including free acid, free base, zwitterionic form, isomorphic crystalline forms, all chiral, enantiomeric, racemic forms, hydrates, solvates, salts and acid salt hydrates, are contemplated to be within the scope of the present invention. The free acid and the sodium, potassium, and calcium salts are the preferred forms.

The peptides of the invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis.

Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 2d. Ed., Wiley & Sons, 1991.

Pharmaceutical kits useful in, for example, the treatment of diabetes, abnormal adipocyte activity, and insulin resistance, which comprise an effective amount of peptides of the invention or pharmaceutically-acceptable salts thereof in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. Such kits may further include, if desired, one or more of various conventional pharmaceutical kit components, such as for example, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

The present invention is further defined in the following Examples, in which all parts and percentages are by weight, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

Synthesis of Monomeric Peptides and Dimeric Peptides

The monomeric peptides (R1 CTF32, R2 CTF32, R1 CTF 30, R1 CTF25, R2 CTF 25, R1 CTF18, R2 CTF18, R1 CTF9, R2 CTF9), homodimeric peptides (R1 CTF32 R1 CTF32, R2 CTF32 R2 CTF32, R1 CTF25 R1 CTF25, R2 CTF25 R2 CTF25), and heterodimeric peptides (R1 CTF32 R2 CTF32, R1 CTF25 R2 CTF25) were synthesized using conventional solid-phase peptide synthesis methodology:
Monomeric Peptide Units

```
(ECM32; R1 CTF32):
                                    SEQ ID NO: 1
VVAAAFVHFYGVSNLQEFRYGLEGGCTDDTLL (R2 CTF32):
                                    SEQ ID NO: 2
VVAGAFVHFHGVSNLQEFRFMIGGGCSEEDAL (R1 CTF30):
                                    SEQ ID NO: 11
HVLVVAAAFVHFYGVSNLQEFRYGLEGGCT (R2 CTF30):
                                    SEQ ID NO: 12
HIFVVAGAFVHFHGVSNLQEFRFMIGGGCS (R1 CTF25):
                                    SEQ ID NO: 5
HFYGVSNLQEFRYGLEGGCTDDTLL (R2 CTF25):
                                    SEQ ID NO: 6
HFHGVSNLQEFRFMIGGGCSEEDAL (R1 CTF18):
                                    SEQ ID NO: 7
LQEFRYGLEGGCTDDTLL (R2 CTF18):
                                    SEQ ID NO: 8
LQEFRFMIGGGCSEEDAL (R1 CTF9):
                                    SEQ ID NO: 9
GGCTDDTLL (R2 CTF9):
                                    SEQ ID NO: 10
GGCSEEDAL
```

Homodimeric Peptides (monomeric units are connected via a disulfide linkage between the cysteine in the first mer unit and the cysteine in the second mer unit)

```
SEQ ID NO: 1 linked to SEQ ID NO: 1
(R1 CTF32 R1 CTF32):

VVAAAFVHFYGVSNLQEFRYGLEGGCTDDTLL
                                    |
        VVAAAFVHFYGVSNLQEFRYGLEGGCTDDTLL
SEQ ID NO: 2 linked to SEQ ID NO: 2
(R2 CTF32 R2 CTF32):

VVAGAFVHFHGVSNLQEFRFMIGGGCSEEDAL
                                    |
        VVAGAFVHFHGVSNLQEFRFMIGGGCSEEDAL
SEQ ID NO: 5 linked to SEQ ID NO: 5
(R1 CTF25 R1 CTF25):

HFYGVSNLQEFRYGLEGGCTDDTLL
                            |
        HFYGVSNLQEFRYGLEGGCTDDTLL
SEQ ID NO: 6 linked to SEQ ID NO: 6
(R2 CTF25 R2 CTF25):

HFHGVSNLQEFRFMIGGGCSEEDAL
                            |
        HFHGVSNLQEFRFMIGGGCSEEDAL
```

Heterodimeric Peptides (monomeric units are connected via a disulfide linkage between the cysteine in the first mer unit and the cysteine in the second mer unit)

SEQ ID NO: 1 linked to SEQ ID NO: 2
(R1 CTF32 R1 CTF32):

```
        VVAAAFVHFYGVSNLQEFRYGLEGGCTDDTLL
                       |
        VVAGAFVHFHGVSNLQEFRFMIGGGCSEEDAL
```

SEQ ID NO: 5 linked to SEQ ID NO: 6
(R1 CTF25 R1 CTF25):

```
            HFYGVSNLQEFRYGLEGGCTDDTLL
                       |
            HFHGVSNLQEFRFMIGGGCSEEDAL
```

SEQ ID NO: 1 linked to SEQ ID NO: 5
(R1 CTF32 R1 CTF25):

```
        VVAAAFVHFYGVSNLQEFRYGLEGGCTDDTLL
                       |
            HFYGVSNLQEFRYGLEGGCTDDTLL
```

SEQ ID NO: 1 linked to SEQ ID NO: 6
(R1 CTF32 R2 CTF25):

```
        VVAAAFVHFYGVSNLQEFRYGLEGGCTDDTLL
                       |
            HFHGVSNLQEFRFMIGGGCSEEDAL
```

SEQ ID NO: 2 linked to SEQ ID NO: 5
(R2 CTF32 R1 CTF25):

```
        VVAGAFVHFHGVSNLQEFRFMIGGGCSEEDAL
                       |
            HFYGVSNLQEFRYGLEGGCTDDTLL
```

SEQ ID NO: 2 linked to SEQ ID NO: 6
(R2 CTF32 R2 CTF25):

```
        VVAGAFVHFHGVSNLQEFRFMIGGGCSEEDAL
                       |
            HFHGVSNLQEFRFMIGGGCSEEDAL
```

Standard synthesis protocols based on Fmoc chemistry were used to prepare the monomeric peptides, which are in turn used to prepare the dimeric peptides. After synthesis, the crude peptides were cleaved from the solid support and side-chain protecting groups were removed. The crude peptides were purified by C18 reverse-phase HPLC using Varian SD-2 Instrument. The peptides were eluted with a gradient of Buffer B for 30 minutes (Buffer A: aqueous phase with 0.1% TFA, pH 2.5 and Buffer B: acetonitrile; flow rate 600 ml/min and detection at 230 mm). The purified peptide were further desalted by HPLC and lyophilized to dry form. The peptides were characterized by analytical HPLC analysis and mass spectrometry analysis, and then packed in sealed vials filled with nitrogen.

To form the homodimeric or heterodimeric peptides, the appropriate monomeric peptide is first formed and then thiol groups of the cysteine units in each monomeric peptide is oxidized to form a disulfide bond.

If there is more than one cysteine in a mer unit, all of the cysteines may be oxidized to form thermodynamically stable products by scrambling with a suitable oxidative reagent in a batch process. Alternatively, if there is more than one cysteine in a mer unit, the desired pair of cysteines (one from the first mer unit and the other from the second mer unit) is formed selectively at a time while any other cysteines are still protected. Suitable oxidative reagents to convert the two thiols to a disulfide bond include, but are not limited to, oxygen (air), dimethyl sulfoxide, oxidized glutathione, potassium ferricyanide, thallium(III) trifluoroacetate. trans-[Pt(en)$_2$Cl$_2$]$^{2+}$ may be used for the quantitative formation of intra-molecular disulfide bonds in peptides [*J. Am. Chem. Soc.*, (2001), 122, 6809-6815].

The dimers of the dimers are formed via an association reaction (hydrogen bonding) between the various mer units of the dimers. For example, for a dimer of a heterodimer, there is an association between the R1 CTF mer and the R2 CTF mer that holds the two dimers in a preferred binding orientation. The association reaction occurs naturally in plasma at physiological pH conditions. The dimers of the dimers may be formed by adjusting the pH of the solution to physiological blood pH conditions, i.e., at about pH 7.4.

Example 2

Proof of Heterodimer

The presence of heterodimer R1 CTF32 R2 CTF32 (SEQ ID NO:1 linked to SEQ ID NO:2) in clinical samples was determined using ELISA testing with antibodies specific for either R1 CTF32 (SEQ ID NO:1) or R2 CTF32 (SEQ ID NO:2). ELISA plates were coated with monoclonal antibody for R1 CTF25 (SEQ ID NO:5). This monoclonal antibody does not capture the R2 CTF32 (SEQ ID NO:2). The analyte bound was detected with a second polyclonal antibody. This experiment was done twice; once with a polyclonal antibody that detected the R1 CTF32 (SEQ ID NO:1) and another time with a polyclonal antibody that detected the R2 CTF32 (SEQ ID NO:2). Neither antibody cross-reacted with the other receptor fragment.

Example 3

Inhibition of Enzymes

Inhibition of insulin degradation enzyme (IDE) is a biological function of CTF. The inhibition reduces insulin degradation in the liver and other tissues and thereby increases insulin levels in the blood. The enzymes for cleavage of the dimers are also potential therapeutic targets. Each of the peptides synthesized in Example 1 was tested for their effect on cleavage and target enzymes (ADAM-17 and IDE at level of 400 ng/ml). The results are shown in TABLE 2 below:

TABLE 2

| Units | Description | ADAM-17 Inhibition (observed) | IDE Inhibition (90% inhibition at) |
|---|---|---|---|
| Monomer | R1 CTF30 | Negative | Negative |
| Monomer | R1 CTF32 | Positive | 50.0 µg/ml |
| Monomer | R1 CTF25 | Negative | 12.4 µg/ml |
| Monomer | R1 CTF17 | Negative | negative |
| Monomer | R1 CTF9 | Negative | negative |
| Monomer | R2 CTF32 | Positive | 40.0 µg/ml |
| Monomer | R2 CTF25 | Negative | 9.0 µg/ml |
| Monomer | R2 CTF9 | Negative | Negative |
| Homodimer | R1 CTF32 R1 CTF32 | Positive | 22.5 µg/ml |
| Homodimer | R2 CTF32 R2 CTF32 | Positive | 19.0 µg/ml |
| Heterodimer | R1 CTF32 R2 CTF32 | Positive | 1.2 µg/ml |
| Heterodimer | R1 CTF25 R2 CTF25 | Negative | 0.6 µg/ml |

Figure 2:
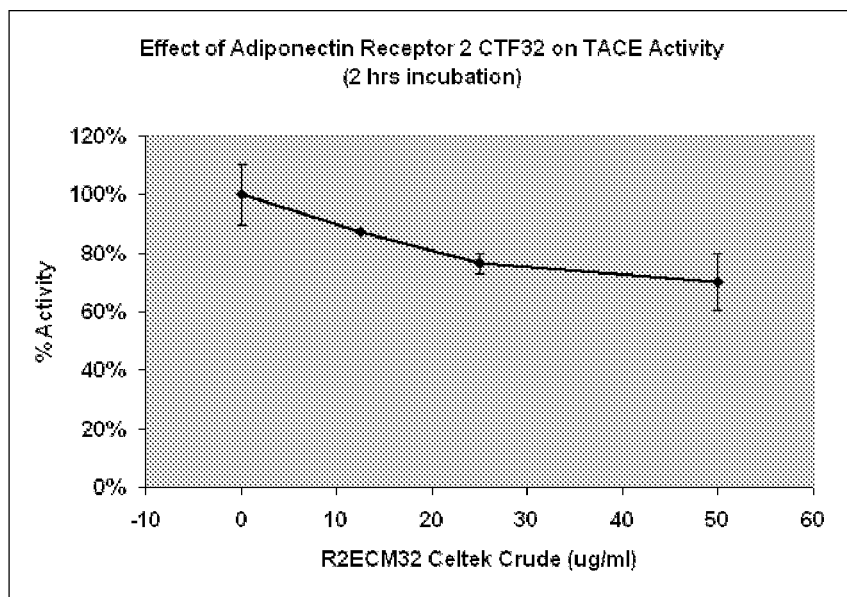
FIG. 2 is a plot of TACE/ADAM-17 activity as a function of the level of R2 CTF32 (SEQ ID NO:2) with a two hour incubation.

The data in TABLE 2 shows that the homodimers and heterodimers of CTF inhibit ADAM-17 and inhibit IDE. The data further shows that the heterodimer (R1 CTF32 R2 CTF32) was more active than the corresponding homodimers (R1 CTF32 R1 CTF32 and R2 CTF32 R2 CTF32). This is unexpected because the homology between R1 CTF32 and R2 CTF32 is very high and no large reactivity differences were observed between R1 CTF32 and R2 CTF32), with the data for the effect of IDE activity and TACE activity for R2 CTF32 shown in FIG. 1 and FIG. 2.

Example 4

Testing of Diabetic Patients

Figure 3:
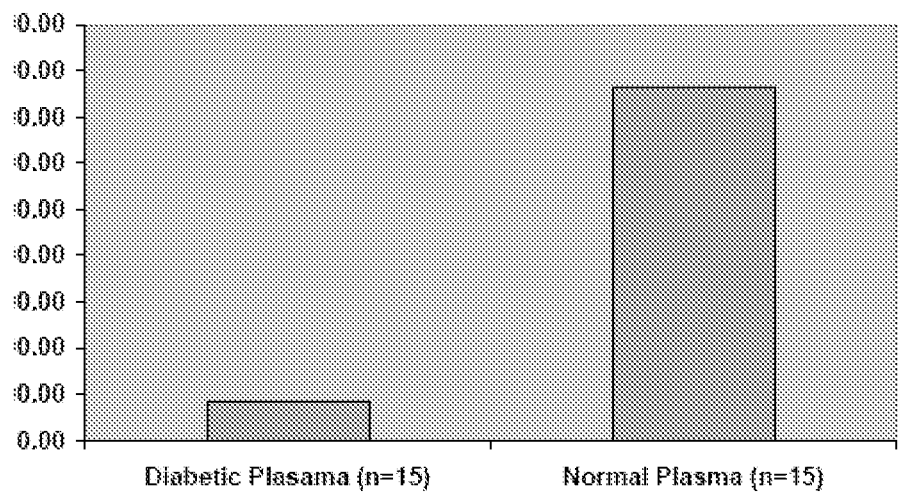
FIG. 3 shows the results from Example 4 of the assay for R1 CTF32 (SEQ ID NO:1) using the R1 CTF 32 monoclonal antibody and the R1 CTF32 polyclonal antibody described in Example 2 to determine plasma levels of R1 in diabetic and normal patients. This assay detects any forms of R1 forms whether monomeric, dimeric, or bound.

The assay for R1 CTF32 (SEQ ID NO:1) using the R1 CTF 32 monoclonal antibody and the R1 CTF32 polyclonal antibody described in Example 2 was used to determine plasma levels of R1 in diabetic and normal patients. This assay detects any forms of R1 forms whether monomeric, dimeric, or bound. The results are shown in FIG. 3.

Figure 4:
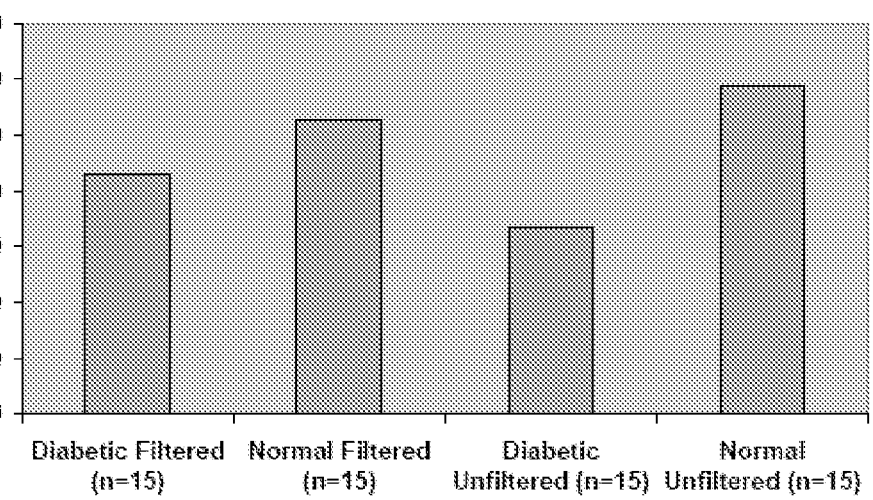
FIG. 4 shows the results from Example 4 of the assay for R1 CTF32 R2 CTF32 (SEQ ID NO:1 linked to SEQ ID NO:2) using the R1 CTF 32 monoclonal antibody and the R2 CTF32 polyclonal antibody described in Example 2 to determine plasma levels of heterodimeric R1 CTF32 R2 CTF32 in diabetic and normal patients. This assay does not detect monomeric form and would only detect heterodimeric form.

The assay for R1 CTF32 R2 CTF32 (SEQ ID NO:1 linked to SEQ ID NO:2) using the R1 CTF 32 monoclonal antibody and the R2 CTF32 polyclonal antibody described in Example 2 was used to determine plasma levels of heterodimeric R1 CTF32 R2 CTF32 in diabetic and normal patients. This assay does not detect monomeric form and would only detect heterodimeric form. Filtering of the samples to remove other proteins binding the heterodimeric R1 CTF32 R2 CTF32 did not impact the results. The results are shown in FIG. 4.

When ranges are used herein for physical properties, such as molecular weight, or chemical properties, such as chemical formulae, all combinations, and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

---

What is claimed is:

1. A method of treating insulin resistance in a patient in need thereof, comprising: administering to said patient an effective amount of a peptide or a pharmaceutically-acceptable salt thereof; wherein said peptide is a heterodimer comprising a first mer unit and a second mer unit, wherein said peptide is a heterodimer comprising a first mer unit and a second mer unit, wherein said first mer unit consists of 25 amino acids and has at least about 75% identity with SEQ ID NO:5 and wherein said second mer unit consists of 25 amino acids and has at least about 75% identity with SEQ ID NO:6, and wherein said first mer unit and said second mer unit are linked via a disulfide bond; or a dimer of said heterodimer.

2. A method of inhibiting insulin degradation enzyme (IDE) in a patient suffering from insulin resistance, comprising: administering to said patient a peptide or a pharmaceutically-acceptable salt thereof in an effective amount to inhibit IDE;
wherein said peptide is a heterodimer comprising a first mer unit and a second mer unit, wherein said first mer unit consists of 25 amino acids and has at least about 75% identity with SEQ ID NO:5 and wherein said second mer unit consists of 25 amino acids and has at least about 75% identity with SEQ ID NO:6, and wherein said first mer unit and said second mer unit are linked via a disulfide bond; or a dimer of said heterodimer.

* * * * *